US008629174B2

(12) United States Patent
Cavalieri et al.

(10) Patent No.: US 8,629,174 B2
(45) Date of Patent: Jan. 14, 2014

(54) UNIFYING MECHANISM AND METHODS TO PREVENT CANCER AND NEURODEGENERATIVE DISEASES

(75) Inventors: Ercole L. Cavalieri, Waterloo, NE (US); Eleanor G. Rogan, Omaha, NE (US)

(73) Assignee: Prevention L.L.C., Waterloo, NE (US)

( * ) Notice: Subject to any disclaimer, the term of this patent is extended or adjusted under 35 U.S.C. 154(b) by 422 days.

(21) Appl. No.: 12/533,883

(22) Filed: Jul. 31, 2009

(65) Prior Publication Data
US 2009/0312391 A1   Dec. 17, 2009

Related U.S. Application Data

(63) Continuation of application No. 10/940,600, filed on Sep. 14, 2004, now abandoned, which is a continuation-in-part of application No. PCT/US03/07686, filed on Mar. 12, 2003.

(60) Provisional application No. 60/364,544, filed on Mar. 14, 2002.

(51) Int. Cl.
*A61K 31/40* (2006.01)
*A61K 31/19* (2006.01)
*A61K 31/05* (2006.01)

(52) U.S. Cl.
USPC .......................... 514/418; 514/557; 514/734

(58) Field of Classification Search
USPC .......................... 514/418, 557, 734
See application file for complete search history.

(56) References Cited

U.S. PATENT DOCUMENTS

| 4,309,415 | A | | 1/1982 | Horrobin |
| 4,827,016 | A | | 5/1989 | Morgan |
| 4,855,305 | A | * | 8/1989 | Cohen .......................... 514/171 |
| 5,084,481 | A | | 1/1992 | Ulrich et al. |
| 5,804,168 | A | | 9/1998 | Murad |
| 6,008,260 | A | * | 12/1999 | Pezzuto et al. ................ 514/733 |
| 6,048,886 | A | | 4/2000 | Neigut |
| 6,264,995 | B1 | | 7/2001 | Newmark et al. |
| 2005/0164911 | A1 | | 7/2005 | Cavalieri et al. |

FOREIGN PATENT DOCUMENTS

| WO | WO-9959561 A2 | 11/1999 |
| WO | WO00/48594 | * 8/2000 |

OTHER PUBLICATIONS

DeFlora et al., Journal of Cellular Biochemistry, 1995;suppl 22:33-41.*
Berstein, L., et al., "Switching (Overtargeting) of Estrogen Effects and its Potential Role in Hormonal Carcinogenesis", *Neoplasma*, 49, (2002), 21-25.
Deigner, H. P, et al., "Apoptosis Modulator in the Therapy of Neurodegenerative Diseases", *US National Library of Medicine*, 9, (2000), 747-764.
"U.S. Appl. No. 10/940,600, Final Office Action mailed Apr. 27, 2009", 7 Pgs.

(Continued)

*Primary Examiner* — San-Ming Hui
(74) *Attorney, Agent, or Firm* — Schwegman, Lundberg & Woessner, P.A.

(57) ABSTRACT

The present invention relates to methods for preventing the development of cancer or neurodegenerative diseases by administering N-Acetylcysteine (NAC), melatonin, or a combination thereof. The present invention also relates to methods for diagnosing cancer and/or neurdegenerative disease by detecting or determining the amount of dopamine metabolites, 4-CE, 2-CE, methylation of CE or CE-Q conjugates.

6 Claims, 14 Drawing Sheets

(56) References Cited

OTHER PUBLICATIONS

"U.S. Appl. No. 10/940,600, Advisory Action mailed Aug. 20, 2009", 3 pgs.

"U.S. Appl. No. 10/940,600, Non-Final Office Action mailed Oct. 8, 2008", 9 pgs.

"U.S. Appl. No. 10/940,600, Preliminary Amendment mailed Mar. 29, 2005", 12 pgs.

"U.S. Appl. No. 10/940,600, Response filed Jun. 29, 2009 to Final Office Action mailed Apr. 27, 2009", 8 pgs.

"U.S. Appl. No. 10/940,600, Response filed Jul. 11, 2008 to Restriction Requirement mailed Jun. 12, 2008", 6 pgs.

"U.S. Appl. No. 10/940,600, Response filed Dec. 9, 2008 to Non Final Office Action mailed Oct. 8, 2008", 8 pgs.

"U.S. Appl. No. 10/940,600, Restriction Requirement mailed Jun. 12, 2008", 7 pgs.

"International Application Serial No. PCT/US03/07686, International Preliminary Report on Patentability mailed Jan. 14, 2005", 8 pgs.

"International Application Serial No. PCT/US03/07686, International Search Report mailed Aug. 27, 2003", 4 pgs.

Zahid, M, et al., "Inhibition of depurinating estrogen-DNA adduct formation by natural compounds.", Chem Res Toxicol., 20(12), (Dec. 2007), 1947-53.

* cited by examiner

C

| | | | | | | |
|---|---|---|---|---|---|---|
| *Anti*-DB[*a,l*]PDE Day 1 | T / C / 39 | G G / A / 93 | | G G CG / A TC / 357 366 364 | C / T / 477 | 8/65 |
| *Anti*-DB[*a,l*]PDE Day 2 | T T / G / 28 | G A / A C / 92 102 | A / C / 127 | G / A / 178 | T G A / G A G / 393 413 400 | T / G / 499 | 10/32 |
| *Anti*-DB[*a,l*]PDE Day 3 | G / C / 39 | C G / G A / 75 92 | | | G T C / A G T / 359 378 399 | | 8/19 |
| *Anti*-DB[*a,l*]PDE Day 4 | | | | | T C T A / T A G / 362 391 419 | | 3/13 |

Nucleotide 1     111     321     500
Codon   1   Exon 1   37   H-*ras*   38   Exon 2   97

D

| | | | | | | | | | |
|---|---|---|---|---|---|---|---|---|---|
| *Anti*-DB[*a,l*]PDE pWT-TDG | A / G / 25 | C / T / 62 | G / A / 92 | | T / C / 291 | G / A / 379 | | | 5/39 |
| *Anti*-DB[*a,l*]PDE Day 1 -TDG | | | | | G / A / 322 | G T CC / A G TT / 402 435 453 455 | | | 5/36 |
| DB[*a,l*]P Day 1 -TDG | T / G / 38 | | CA G / TG A / 200 221 203 | T / T / | T / A / 391 | TA / AG / 436 437 | | | 9/35 |
| DB[*a,l*]P Day 2 -TDG | T T T T / G / 38 | T / C / 60 | C / T / 113 | G / A / 162 | T T T T T G / C A / 285 322 | G / A / 355 | T T / A / 391 | G T GTT C / A C G T / 408 435 426 460 | 22/33 |
| DB[*a,l*]P Day 3 -TDG | TC GT / 38 41 | C / T / 68 | C / T / 84 | C G C / T A T / 142 161 193 | T / C / 283 | G C / A T / 333 350 | T T T / T A / 391 | G T T / G A / 435 463 | 25/36 |

Nucleotide 1     111     321     500
Codon   1   Exon 1   37   H-*ras*   38   Exon 2   97

Fig. 4 Continued

| Sequence | Mutation (nt) |
|---|---|
| CTGGAGGCGTG | C (37) |
| TGTGGACGAGT | G (89) |
| TGACCAAACAG | G (169) |
| TGGGGTATGAT | C (200) |
| GTGCAAGGGTG | G (228) |
| TGCAAAACAAC | G (314) |
| TTGCAGGACTC | C (320) |
| TGGGGAGACAT | G (355) |
| ATGTCTACTGG | C (364) |
| AGAGTATAGTG | G (400) |
| CATCAACAACA | G (463) |

SEQUENCE LISTING

```
<160> NUMBER OF SEQ ID NOS: 11

<210> SEQ ID NO 1
<211> LENGTH: 11
<212> TYPE: DNA
<213> ORGANISM: Artificial Sequence
<220> FEATURE:
<223> OTHER INFORMATION: A synthetic oligonucleotide

<400> SEQUENCE: 1
ctggaggcgt g                                                          11

<210> SEQ ID NO 2
<211> LENGTH: 11
<212> TYPE: DNA
<213> ORGANISM: Artificial Sequence
<220> FEATURE:
<223> OTHER INFORMATION: A synthetic oligonucleotide

<400> SEQUENCE: 2
tgtggacgag t                                                          11

<210> SEQ ID NO 3
<211> LENGTH: 11
<212> TYPE: DNA
<213> ORGANISM: Artificial Sequence
<220> FEATURE:
<223> OTHER INFORMATION: A synthetic oligonucleotide

<400> SEQUENCE: 3
tgaccaaaca g                                                          11

<210> SEQ ID NO 4
<211> LENGTH: 11
<212> TYPE: DNA
<213> ORGANISM: Artificial Sequence
<220> FEATURE:
<223> OTHER INFORMATION: A synthetic oligonucleotide

<400> SEQUENCE: 4
tggggtatga t                                                          11
```

```
<210> SEQ ID NO 5
<211> LENGTH: 11
<212> TYPE: DNA
<213> ORGANISM: Artificial Sequence
<220> FEATURE:
<223> OTHER INFORMATION: A synthetic oligonucleotide

<400> SEQUENCE: 5
gtgcaagggt g                                                            11

<210> SEQ ID NO 6
<211> LENGTH: 11
<212> TYPE: DNA
<213> ORGANISM: Artificial Sequence
<220> FEATURE:
<223> OTHER INFORMATION: A synthetic oligonucleotide

<400> SEQUENCE: 6
tgcaaaacaa c                                                            11

<210> SEQ ID NO 7
<211> LENGTH: 11
<212> TYPE: DNA
<213> ORGANISM: Artificial Sequence
<220> FEATURE:
<223> OTHER INFORMATION: A synthetic oligonucleotide

<400> SEQUENCE: 7
ttgcaggact c                                                            11

<210> SEQ ID NO 8
<211> LENGTH: 11
<212> TYPE: DNA
<213> ORGANISM: Artificial Sequence
<220> FEATURE:
<223> OTHER INFORMATION: A synthetic oligonucleotide

<400> SEQUENCE: 8
tggggagaca t                                                            11

<210> SEQ ID NO 9
<211> LENGTH: 11
<212> TYPE: DNA
<213> ORGANISM: Artificial Sequence
<220> FEATURE:
<223> OTHER INFORMATION: A synthetic oligonucleotide

<400> SEQUENCE: 9
atgtctactg g                                                            11

<210> SEQ ID NO 10
<211> LENGTH: 11
<212> TYPE: DNA
<213> ORGANISM: Artificial Sequence
<220> FEATURE:
<223> OTHER INFORMATION: A synthetic oligonucleotide

<400> SEQUENCE: 10
agagtatagt g                                                            11
```

```
<210> SEQ ID NO 11
<211> LENGTH: 11
<212> TYPE: DNA
<213> ORGANISM: Artificial Sequence
<220> FEATURE:
<223> OTHER INFORMATION: A synthetic oligonucleotide

<400> SEQUENCE: 11
catcaacaac a                                                              11
```

UNIFYING MECHANISM AND METHODS TO PREVENT CANCER AND NEURODEGENERATIVE DISEASES

RELATED APPLICATION

This application is continuation of U.S. application Ser. No. 10/940,600, filed Sep. 14, 2004, which is a continuation-in-part of PCT/US03/07686, filed Mar. 12, 2003 (which published in English on Sep. 25, 2003 as WO 03/077900) which claims priority to U.S. Provisional Application Ser. No 60/364,544 filed Mar. 14, 2002, which applications and publication are herein incorporated by reference.

GOVERNMENT FUNDING

The invention described herein was made with government support under Grant Number PO1CA49210 and RO1CA49917 awarded by the National Cancer Institute, NIH. The United States Government has certain rights in the invention.

BACKGROUND OF THE INVENTION

Cancer is a disease that begins with mutation of critical genes: oncogenes and tumor suppressor genes. Mutation of critical genes allows for a cancer cell to evolve and ultimately results in pathogenic replication (a loss of normal regulatory control leading to excessive cell proliferation) of various given types of cells found in the human body. Conventional cancer treatments have focused mainly on killing cancerous cells. Such treatments threaten noncancerous cells, inherently are stressful to the human body, produce many side effects, and are of uncertain efficacy. More important, such treatment regimens are not necessarily directed toward the actual root of the cancer problem or its prevention.

Other diseases are associated with excessive cell death. For example, diseases associated with the loss of neurons in different regions of the central nervous system (CNS), including, for example, brain tissue and the spinal cord, such as Alzheimer's disease, amyotrophic lateral sclerosis ("ALS" or "Lou Gehrig's disease"), Parkinson's disease, Huntington's disease, brain aging, Friedreich's ataxia, multiple sclerosis, diabetic necrosis, ischaemia, and stroke. These types of diseases are exemplary of diseases and disorders collectively referred to as "neurodegenerative diseases." Treatment and prevention of neurodegenerative disorders remains elusive in that many proposed treatment methods are not practical since exogenous administration of numerous putative therapeutics is not efficacious due to their general inability to cross the blood-brain barrier.

Thus, there is a need in the art for therapeutic methods to prevent or reduce the risk of the development of cancer and/or the development of neurodegenerative diseases.

SUMMARY OF THE INVENTION

Applicant has discovered that oxidation of the carcinogenic 4-hydroxy catechol estrogens (CE) of estrone ($E_1$) and estradiol ($E_2$) to catechol estrogen-3,4-quinones (CE-3,4-Q) results in electrophilic intermediates that covalently bind to DNA to form depurinating adducts at the N-7 of guanine and N-3 of adenine by 1,4-Michael addition. The resultant apurinic sites in critical genes can generate mutations that may initiate various human cancers. As such, the endogenous quinones, including CE-3,4-Q, may be endogenous tumor initiators. As yet, there are no treatment methods available that are specifically directed toward preventing the association of the metabolic intermediates, such as endogenous (that which has originated or been produced within an organism, tissue, or cell) quinones, with DNA, and thus, preventing excessive cell growth and the development/formation of cancer.

Applicant has also discovered that the catecholamine dopamine and the metabolite catechol (1,2-dihydroxybenzene) of the leukemogenic benzene can be oxidized to their quinones which react with DNA to form predominantly analogous depurinating adducts. In the case of depurinating adducts resulting from oxidization of dopamine to its quinone, the resultant apurinic sites in critical genes can generate mutations that may initiate brain cancer and/or neurodegenerative diseases.

Therefore, Applicant has discovered that apurinic sites formed by depurinating adducts are converted into tumor-initiating or neurodegenerative-initiating mutations by error-prone repair. Thus, Applicant has discovered a unifying molecular mechanism of initiation for many cancers and neurodegenerative diseases. Using this unifying molecular mechanism, Applicant has also designed strategies to assess risk and to prevent such diseases.

Applicant has also discovered that N-acetylcysteine (NAC) is capable preventing the formation of depurinating adducts (endogenous tumor initiators and/or neurodegenerative initiators) by aiding in the removal, detoxification and/or sequestration of, for example, catechol quinones and/or the oxidation products of benzene and dopamine prior to their association with DNA. Applicant has further discovered that NAC may be useful to prevent the formation of quinones.

Applicant has further discovered that melatonin is useful in the prevention of the formation of depurinating adducts, particularly those formed in the brain due to dopamine oxidation and the resultant production of its quinone.

Thus, Applicant has discovered that the use of NAC and/or melatonin can prevent or diminish the formation of depurinating adducts, and therefore, prevent and/or treat cancer and/or neurodegenerative disorders. Further, it is believed that practice of the invention will, at least in part, influence and control cellular mortality by allowing the cell to maintain a lower level of endogenous quinones (that have the ability to bind DNA and form depurinating adducts) and thus, allow the cell to follow a normal apoptotic pathway (programmed cell death, such as that signaled by the nuclei in normally functioning human and animal cells when age or state of cell health and condition dictates).

Accordingly, the present invention provides pharmaceutical compositions and methods to treat and/or prevent cancer and neurodegenerative diseases and for reducing cancer and neurodegenerative disease mortality. The present invention is further directed to methods of utilizing N-acetylcysteine (NAC) and melatonin to treat, prevent, and/or reduce the risk of cancer and neurodegenerative diseases and disorders, to reduce the formation of DNA adducts by reactive electrophilic estrogen metabolites, and/or to reduce the formation of DNA adducts by reactive electrophilic dopamine metabolites.

The present invention also relates to a therapeutic method of preventing, treating or reducing the risk of a pathological condition or symptom in a mammal, including a human, which is suffering or may suffer from said condition, wherein production of quinones is implicated and antagonism of such production or removal of such quinones is desired, comprised of administering to a mammal an effective amount of NAC, melatonin, a physiologically acceptable salt thereof, or a combination thereof. Therefore, the present invention provides a method for modulating quinone production (e.g., CE-3,4-Q or the quinone of dopamine) or altering the amount of quinones present in a mammal. Also provided is a therapeutic method for preventing or treating a pathological condition or symptom in a mammal, such as a human, wherein the production of depurinating DNA adducts from the action of endogenous quinones is implicated and antagonism of such action is desired, comprised of administering to a mammal in need of such therapy, an effective amount of NAC, melatonin, a pharmaceutically acceptable salt thereof, or a combination thereof.

Further provided is a method of treating or preventing a neoplastic or neurodegenerative condition or both conditions in a subject comprising administering an effective amount of NAC, melatonin, a physiologically acceptable salt thereof, or a combination thereof. The combination treatment method provides for simultaneous, sequential or separate use in treating such conditions.

The present invention also relates to a method for identifying an agent useful to prevent, reduce the risk, or treat cancer comprised of contacting a host cell with $E_2$ and a candidate agent and determining whether the candidate agent reduces the amount of CE-3,4-Q or depurinating adducts in the cell compared to a control. Another method for identifying an agent useful to prevent or reduce the risk of cancer or neurodegenerative disease comprises incubating DNA with a catechol estrogen quinone or a catecholamine dopamine quinone and a candidate agent and determining whether the candidate agent reduces the association of the quinone with DNA. The invention also provides agents identified by such methods.

Also provided is a method for determining the risk of developing cancer or a neurodegenerative disease in a mammal comprising determining the amount of endogenous quinone present in a biological test sample, such as blood, urine or other body fluid (including spinal fluid) or a tissue biopsy, and comparing the determined amount to an amount present in a normal sample, wherein an increase in amount of quinone correlates with the risk of developing cancer (e.g., breast cancer), and/or a neurodegenerative disease.

The invention further provides a method for detecting cancer and/or neurodegenerative disease in a mammal, preferably a human. The method comprises subjecting a physiological sample from a human to analytical detection to determine the presence or amount of dopamine metabolites (such as dopamine quinones), 4-CE, 2-CE, methylation of CE and/or CE-Q conjugates. The presence or amount of dopamine metabolites, 4-CE, 2-CE, methylation of CE and/or CE-Q conjugates is then compared to an amount present in a control sample, wherein an increase in the amount of dopamine metabolites, 4-CE, methylation of CE and/or CE-Q conjugates correlates to the presence or absence of cancer and/or neurodegenerative disease. Also provided is a diagnostic method for detecting dopamine metabolites, 4-CE, 2-CE, methylation of CE and/or CE-Q conjugates.

The presence or amount of dopamine metabolites, 4-CE, 2-CE, methylation of CE and/or CE-Q conjugates that changes over time can indicate the progression or remission of cancer, such as breast cancer, or neurodegenerative disease, as well as the presence of previously undiagnosed metastatic or neurodegenerative disease. Thus, the present invention provides a method for monitoring the course, progression or remission of cancer, such as breast cancer, and neurodegenerative disease. This method comprises analyzing a physiological sample by analytical methods. The presence or amount of dopamine metabolites, 4-CE, 2-CE, methylation of CE and/or CE-Q conjugates is detected or determined. At least one point later in time, another sample is taken and the amount of dopamine metabolites, 4-CE, 2-CE, methylation of CE and/or CE-Q conjugates is determined. The amounts of dopamine metabolites, 4-CE, 2-CE, methylation of CE and/or CE-Q conjugates, obtained at least at two different time points, are compared.

The methods of the invention also optionally comprise administering an agent that induces the protective enzyme quinone reductase.

The methods of the invention also optionally comprise administering an agent that inhibits CYP1B1.

The methods of the invention also optionally comprise administering lipoic acid or a pharmaceutically acceptable salt thereof.

The methods of the invention also optionally comprise administering resveratrol or a pharmaceutically acceptable salt thereof.

The methods of the invention also optionally comprise administering lipoic acid and resveratrol or pharmaceutically acceptable salts thereof.

The present invention also provides pharmaceutical compositions which comprise an effective amount of NAC and an effective amount of melatonin or a physiologically acceptable salt thereof, together with one or more physiologically acceptable carriers or excipients. Such a composition is useful, for example, to treat and/or prevent cancer and/or neurodegenerative diseases, as well as other diseases that are effected by the activity of quinones (e.g., formation of genetic lesions). The invention also provides a pharmaceutical composition comprising 1) NAC or a physiologically acceptable salt thereof, 2) melatonin or a physiologically acceptable salt thereof, 3) optionally one or more agents that induce quinone reductase, and 4) one or more physiologically acceptable carriers or excipients. The compositions of the invention can also optionally comprise an agent that inhibits CYP1B1.

The invention also provides the use of NAC and/or melatonin to prepare a medicament useful to treat cancer and/or neurodegenerative diseases.

BRIEF DESCRIPTION OF THE FIGURES

FIG. 6 demonstrates sequence similarity among sites of DB[a,l]P-induced mutations in H-ras DNA of mouse skin at day 1 (SEQ ID NOs: 1-11). A putative conserved sequence is shaded. The mutated base is underlined. The italicized sequence ($A^{314} \rightarrow G$ mutation) is from the bottom strand.

FIGS. 7A-C depict H-ras mutations induced by $E_2$-3,4-Q. (A) PCR artifact mutations induced in untreated skin DNA and in a cloned H-ras gene (pWT) treated with $E_2$-2,3-Q or with $E_2$-3,4-Q. (B) H-ras mutations in mouse skin DNA after treatment with 200 nmol $E_2$-3,4-Q in 100 mL of acetone/ethanol (70:30). The spectra contained mostly A/T to G/C mutations. (C) H-ras mutations after TDG treatment of DNA from $E_2$-3,4-Q-treated mouse skin. TDG treatment resulted in drastic reduction of A/T to G/C mutations in 6 h and 12 h samples, but not in 1 d and 3 d samples. This suggests that these mutations were in the form of G.T heteroduplexes between 6-12 h, but were converted into fixed mutations after that.

DETAILED DESCRIPTION OF THE INVENTION

Figure 1:
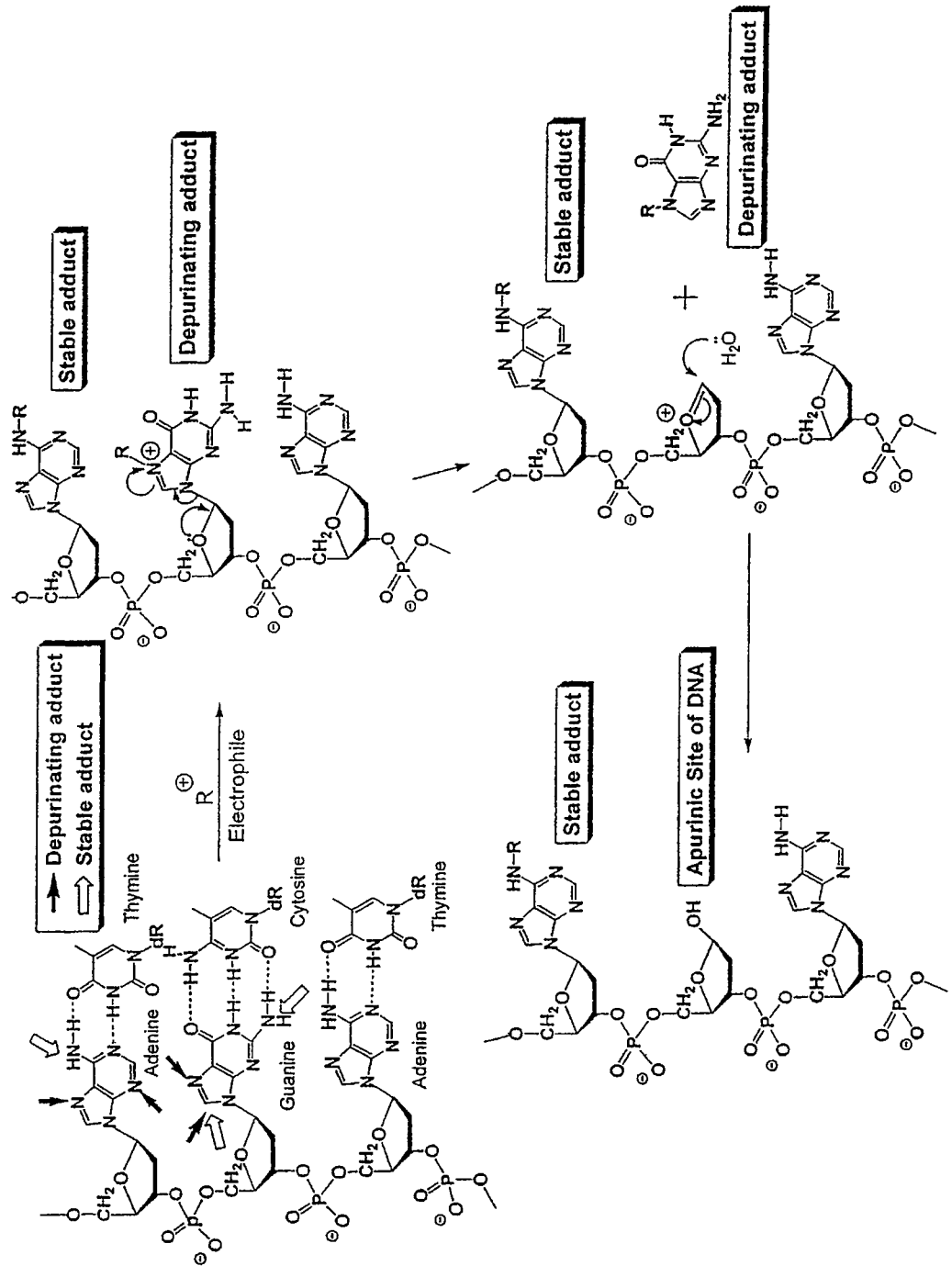
FIG. 1 depicts the formation of stable and depurinating DNA adducts, and generation of apurinic sites.

The present invention is based upon the discovery of a unifying mechanism, namely, formation of catechol quinones and reaction with DNA by 1,4-Michael addition to yield depurinating adducts that could give rise to cancers and/or neurodegenerative diseases. The present invention therefore provides pharmaceutical compositions and methods to prevent and/or treat cancer and/or neurodegenerative diseases resulting from the formation of quinones and/or the reaction of such quinones with DNA by 1,4-Michael addition yielding depurinating adducts.

Compositions of NAC and/or Melatonin for Therapeutic Use

Therapeutic and/or effective amounts of NAC, melatonin, or a combination thereof are amounts which are effective to: prevent the development, further development, or reduce the risk of development of cancer and/or neurodegenerative diseases; reduce the formation of DNA adducts by endogenous reactive electrophilic estrogen metabolites; and/or reduce the formation of DNA adducts by endogenous reactive electrophilic dopamine metabolites. Such effects are achieved while exhibiting little or no adverse effects on normal, healthy tissues or cells or while exerting negligible or manageable adverse side effects on normal, healthy tissues or cells of the mammal.

Administration of NAC and/or melatonin as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

NAC and/or melatonin can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, NAC and/or melatonin may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

NAC and/or melatonin may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, NAC and/or melatonin may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver NAC and/or melatonin to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of NAC and/or melatonin can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of NAC and/or melatonin in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount/preferred dose of NAC, melatonin, an active salt or derivative thereof, or a combination thereof, required for use in treatment will vary not only with the particular salt/composition selected, but also with the route of administration, the nature of the condition being treated and the age, weight and condition of the patient. Importantly, the quantity of NAC, melatonin, an active salt or derivative thereof, or a combination thereof, used should be sufficient to prevent, inhibit, reduce the risk of, or treat cancer and/or prevent, inhibit, reduce the risk of, or treat neurodegeneration. Thus, a variety of clinical factors will influence the preferred dosage ranges and will be ultimately at the discretion of the attendant physician or clinician.

In general, however, a suitable dose of NAC will typically be in the range of from about 0.5 to about 10 mg/kg, e.g., from about 2 to about 10 mg/kg of body weight per day, preferably in the range of 5 to 9 mg/kg/day.

NAC can be conveniently administered in unit dosage form; for example, containing 5 to 1000 mg, conveniently 10 to 750 mg, most conveniently, 50 to 500 mg of active ingredient per unit dosage form.

In general, however, a suitable dose of melatonin will typically be in the range of from about 0.01 to about 0.2 mg/kg, e.g., from about 0.1 to about 0.2 mg/kg of body weight per day, preferably in the range of 0.05 to 0.15 mg/kg/day.

Melatonin can be conveniently administered in unit dosage form; for example, containing 1 to 20 mg, conveniently 2 to 15 mg, most conveniently, 3 to 10 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Methods for Using NAC and/or Melatonin

Through research of the underlying mechanisms of the formation of cancer and the development of neurodegenerative disease or disorders, Applicant has made the unexpected discovery of a unifying molecular mechanism of initiation for many cancers and neurodegenerative diseases. This unifying mechanism involves the oxidation of the carcinogenic 4-hydroxy catechol estrogens (CE) of estrone (E1) and estradiol (E2) to catechol estrogen-3,4-quinones (CE-3,4-Q) resulting in electrophilic intermediates that covalently bind to DNA to form depurinating adducts at the N-7 of guanine and N-3 of adenine by 1,4-Michael addition. It also involves the oxidation of the catecholamine dopamine and the metabolite catechol (1,2-dihydroxybenzene) of the leukemogenic benzene to their quinones which react with DNA to form predominantly analogous depurinating adducts. The resultant apurinic sites in critical genes can generate mutations that may initiate various human cancers and/or neurodegenerative diseases or disorders.

Applicant has discovered that NAC and/or melatonin, both of which may cross the blood-brain barrier, are two agents that reduce the formation of such above-mentioned endogenous quinones. It has also been discovered that NAC and/or melatonin reduce the formation of depurinating adducts due to the action of quinones. As such, administration of NAC or melatonin alone or in combination surprisingly and unexpectantly offers a method for preventing and/or reducing the risk of cancer and/or neurodegenerative diseases.

In a preferred method, compositions comprising NAC and/or melatonin are used for the prevention, inhibition, and/or treatment of cancers such as primary or metastatic melanoma, thymoma, lymphoma, sarcoma, lung cancer, liver cancer, brain cancer, non-Hodgkin's lymphoma, Hodgkins lymphoma, leukemias, uterine cancer, cervical cancer, bladder cancer, rectal cancer, kidney cancer, colon cancer, and adenocarcinomas such as breast cancer, prostate cancer, ovarian cancer, and pancreatic cancer.

In another preferred method, compositions comprising NAC and/or melatonin are used for the prevention, inhibition and/or treatment of neurodegenerative diseases such as diseases associated with the loss of neurons in different regions of the central nervous system (CNS), including, for example, brain tissue and the spinal cord, such as Alzheimer's disease, amyotrophic lateral sclerosis ("ALS" or "Lou Gehrig's disease"), Parkinson's disease, Huntington's disease, brain aging, Friedreich's ataxia, multiple sclerosis, diabetic necrosis, ischaemia, and stroke.

Other Agents

The unifying mechanism that has been discovered also suggests other agents that will be useful for treating or preventing cancer and neurodegenerative diseases. For example, it has been determined that agents that induce the protective enzyme quinone reductase, which reduces catechol estrogen quinones to catechol estrogens, will also provide beneficial effects. Two such agents are lipoic acid and resveratrol. Additionally, agents that inhibit CYP1B1 will also provide a beneficial effect.

Lipoic acid (1,2-dithiolane-3-pentanoic acid) is an antioxidant because the dithiolane structure is a strained five-membered ring that is highly reactive. The relatively high energy content of the disulfide group in lipoic acid makes it reactive with oxidizing molecules. The reduced form of lipoic acid, dihydrolipoic acid (the two forms are in equilibrium) has greater antioxidant activity. Thus, the potent reducing capacity of dihydrolipoic acid and the high reactivity of the disulfide groups in lipoic acid make this couple important as an antioxidant defense system in the cell. The LA/DHLA exhibits free radical (superoxide anion radical and hydroxyl radicals) scavenging properties, reducing oxidative stress. Because it is a strong reductant, it can regenerate vitamin C, Vitamin E and GSH from their oxidized forms. Lipoic acid readily crosses the blood-brain barrier. Finally, it is believed that lipoic acid will induces the protective enzyme quinone reductase, which reduces CEQ back to CE.

Resveratrol, a polyphenolic phytoalexin, is a natural fungicide in more than 70 plant species. It is an antioxidant and an antimutagen. Resveratrol scavenges hydroxyl radicals, superoxide anion radicals and metal-induced radicals, thus protecting against lipid peroxidation. It inhibits cytochrome P450 1A1, 1B1 and 3A4, thus reducing oxidation of estrogens to catechol estrogens (CE). It is also an inducer of quinone reductase, thus increasing the reduction of CEQ to CE. Resveratrol inhibits dioxin-induced expression of P450 1A1 and 1B1, as well as CE-mediated oxidative damage to DNA in cultured human mammary epithelial cells. Resveratrol also inhibits CYP1B1, the major enzyme that catalyzes formation of 4-catechol estrogens in extrahepatic tissues (like the breast, prostate, etc. Inhibition of CYP1B1 activity in the breast, would be expected to lower amounts of 4-CE, lower mounts of CE-3,4-quinones and reduce formation of depurinating 4-CE-DNA adducts that generate mutations leading to the initiation of cancer. Accordingly, the compositions of the invention can optionally comprise one or more agents that induce quinone reductase (e.g. lipoic acid and resveratrol). The compositions of the invention can also optionally comprise one or more agents that inhibit CYP1B1 (e.g. resveratrol). Additionally, the methods of the invention can optionally comprise administering one or more agents that induce quinone reductase. The methods of the invention can also optionally comprise administering one or more agents that inhibit CYP1B1.

Method for Detecting and/or Diagnosing Cancer and/or Neurodegenerative Disease

As described herein below, 4-CE were 3.5 times more abundant than the 2-CE and were 4 times higher than in women without breast cancer, demonstrating that the amount of 4-CE present in a physiological sample correlates with cancer. Additionally, a lower level of methylation was observed for the CE cancer cases compared to controls. Also, CE-Q conjugate levels were 3 times higher in women with cancer than controls. Therefore, the determination of the presence and/or amount of dopamine quinone, 4-CE, 2-CE, methylation of CE and/or CE-Q conjugates may be useful in the diagnosis, treatment and/or monitoring of the progression or remission of cancer, such as breast cancer, and/or neurodegenerative diseases. Thus, there is provided a method for determining the risk of developing cancer and/or a neurodegenerative disease in a mammal comprised of determining the amount of endogenous quinone, dopamine quinone, 4-CE, 2-CE, methylation of CE and/or CE-Q conjugates present in a physiological sample from a mammal, such as blood, urine or other body fluid or a tissue biopsy, and comparing the determined amount to an amount present in a control sample, wherein an increase in amount of quinone correlates with cancer, such as breast cancer, and/or neurodegenerative disease. The presence or quantity of quinone in the sample can be determined using any suitable analytical method, such as IR, UV, NMR, Mass Spec or HPLC. A preferred method for detecting or determining the presence or amount of estrogen metabolites, dopamine metabolites, conjugates and depurinating DNA adducts, including 4-CE, 2-CE, methylation of CE and/or CE-Q conjugates, is by HPLC with electrochemical detection.

Screening Method for Identifying New Therapeutic Agents

The present invention also provides a screening method to identify new therapeutic agents that inhibit the production and/or the activity (e.g., the ability to associate with or bind DNA and form depurinating DNA adducts) of endogenous quinones. Preferably, the quinones have formed endogenously from the oxidation of the carcinogenic 4-hydroxy catechol estrogens (CE) of estrone ($E_1$) and estradiol ($E_2$) to catechol estrogen-3,4-quinones (CE-3,4-Q) resulting in electrophilic intermediates that covalently bind to DNA to form depurinating adducts at the N-7 of guanine and N-3 of adenine by 1,4-Michael addition. The resultant apurinic sites in critical genes can generate mutations that may initiate various human cancers. Also, the quinones may form endogenously from the oxidation of the catecholamine dopamine and the metabolite catechol (1,2-dihydroxybenzene) of the leukemogenic benzene to their quinones which can react with DNA to form predominantly analogous depurinating adducts. In the case of depurinating adducts resulting from oxidization of dopamine to its quinone, the resultant apurinic sites in critical genes can generate mutations that may initiate brain cancer and/or neurodegenerative diseases.

The present invention provides an in vitro binding assay comprising incubating DNA and catechol estrogen quinones or catecholamine dopamine quinones (e.g., for about 2 hours at 37° C.) with and without a candidate agent. After the incubation period, stable adducts are quantified (e.g., by a $^{32}$P-postlabeling method, as used and described hereinbelow, and the presence or quantity of depurinating adducts is analyzed (e.g., by high pressure liquid chromatography, HPLC). The components of the reaction mixture with the candidate agent are compared to those of the reaction mixture without the candidate agent (control) to determine whether the candidate agent is able to inhibit or prevent the association/binding of DNA and quinones and/or the formation of depurinating adducts. If the quantity of DNA/quinone complexes and/or depurinating adducts formed in the reaction mixture with the candidate agent is less than the mixture without the candidate agent, then the candidate agent may be useful in a method for preventing or reducing the risk of cancer and/or neurodegenerative disease.

One cellular screening method comprises contacting a culture of cells (e.g., mammalian cells) with $E_2$, contacting a duplicate culture of cells with a candidate agent and $E_2$, and measuring the effect of the candidate agent on the production of CE-3,4-Q, or depurinating adducts. This screening method can identify agents which block the production of endogenous quinones and/or detoxify them (rendering them unable to produce depurinating adducts).

Another cell model for screening for therapeutic agents comprises contacting tissue cultured cells, such as cancerous tissue (e.g., breast), which has been tested to contain relatively higher than normal amounts of 4-CE or CE-3,4-Q (as determined by analytical methods) with a candidate agent and measuring the effect of the candidate agent on the production of 4-CE, CE-3,4-Q or depurinating adducts. If the amount of 4-CE, CE-3,4-Q, or depurinating adducts is reduced in the treated sample as compared to a control sample, the candidate agent may be useful in a method for preventing or reducing the risk of cancer and/or neurodegenerative diseases.

According to the methods of the invention, a sample can be compared to an appropriate control (e.g., a control mammal or a control cell) the criteria for selecting an appropriate control are well understood by those of skill in the art. For example, a control mammal may be a similar mammal lacking the condition for which you are testing (e.g., cancer (e.g., breast cancer) or neurodegenerative disease).

The compositions and methods of the invention will now be illustrated by the following non-limiting Examples.

Example I

Initiation of Cancer and Other Diseases by Catechol Ortho-Quinones: A Unifying Mechanism Introduction One of the major obstacles in cancer research is that cancer is a problem of 200 diseases. This viewpoint has impeded researchers from looking at the etiology of cancers because the search would be prohibitively complex. For this reason, the etiology of breast, prostate and other human cancers remains virtually unknown. While the expression of various cancers coincides with the above concept, some scientists consider there to be a common, but not yet elucidated, origin for many prevalent types of cancer.

There is widespread agreement in the scientific community that cancer is basically a genetic disease—not in the sense that most cancers are inherited, but in the sense that cancer is triggered by genetic mutations. Thus, cancer can be considered a disease of mutated critical genes that modulate cell growth and death. These include oncogenes and tumor suppressor genes, which give rise to transformation and abnormal cell proliferation. Understanding the origin of these mutations opens the door to strategies for controlling and preventing cancer. (Chakravarti D. et al., *Mutation Res.*, 456, 17-32 (2000) and *Oncogene*, 20:7945-7953 (2001); Weinberg R. A., *Sci. Am.*, 275, 62-77 (1996).)

A second barrier to the progress of cancer research is related to the reluctance of the scientific community to recognize that the natural estrogens, including estrone ($E_1$) and estradiol ($E_2$), are true carcinogens, which induce tumors in various hormone-dependent and independent organs of several animal species and strains. (*International Agency for Research on Cancer Monographs*, 6, 99-132 (1974); *International Agency for Research on Cancer Monographs*, 21, 279-362 (1979); *International Agency for Research on Cancer Monographs*, An updating of IARC monographs volumes 1 to 42 (1987); *IARC Monographs*, Suppl. 7, 272-310).)

A third obstacle to the progress of research on breast and other hormone-dependent cancers is related to the standard paradigm, stated by Feigelson and Henderson, that estrogens, through receptor-mediated processes, "affect the rate of cell division and, thus, manifest their effect on the risk of breast cancer by causing proliferation of breast epithelial cells. Proliferating cells are susceptible to genetic errors during DNA replication, which, if uncorrected, can ultimately lead to a malignant phenotype". While there is no doubt that estrogen-mediated control of cell proliferation plays a role in the development of breast and other hormone-dependent cancers, accumulating evidence suggests that specific oxidative metabolites of estrogens, if formed, can be the endogenous ultimate carcinogens. By reacting with DNA, they cause the mutations leading to cancer. This initiating mechanism occurs in hormone-dependent and independent tissues. (Feigelson H. S. and Henderson B. E., *Carcinogenesis*, 17: 2279-2284 (1996); *JNCI Monograph* 27, E. Cavalieri and E. Rogan (eds.), Oxford Press, Washington (2000).)

Abbreviations

Ade, adenine; BP, benzo[a]pyrene, CE, catechol estrogen(s); CE-Q, catechol estrogen quinone(s); CE-SQ, catechol estrogen semiquinone(s); COMT, catechol-O-methyltransferase; CYP, cytochrome P450; DB[a,l]P, dibenzo[a,l]pyrene; anti-DB[a,l]PDE, anti-dibenzo[a,l]pyrene-11,12-dihydrodiol-13,14-epoxide; DMBA, 7,12-dimethylbenz[a]anthracene; $E_1$, estrone; $E_2$, estradiol; Gua, guanine; GSH, glutathione; H, Harvey; OHE$_2$, hydroxyestradiol; PAH, polycyclic aromatic hydrocarbon(s); PCR-RFLP, polymerase chain reaction-restriction fragment length polymorphism(s); TDG, T.G-DNA glycosylase.

Results and Discussion

Covalent Binding of Carcinogens to DNA: Stable and Depurinating Adducts

Chemical carcinogens covalently bind to DNA to form two types of DNA adducts: stable ones that remain in DNA unless removed by repair and depurinating ones that are released from DNA by destabilization of the glycosyl bond (FIG. 1). Stable adducts are formed when carcinogens react with the exocyclic $N^6$ amino group of adenine (Ade) or $N^2$ amino group of guanine (Gua), whereas depurinating adducts are obtained when carcinogens covalently bind at the N-3 or N-7 of Ade or the N-7 or sometimes C-8 of Gua. The loss of Ade or Gua by depurination leads to formation of apurinic sites that can generate the mutations leading to tumor initiation. (Cavalieri E. L. and Rogan E. G., *Pharmacol. Ther.*, 55, 183-99 (1992); Cavalieri E. L. and Rogan E. G., Mechanisms of tumor initiation by polycyclic aromatic hydrocarbons in mammals, In: The Handbook of Environmental Chemistry: PAHs and Related Compounds, 3J, pp. 81-117, Neilson A. H. (ed.), Springer, Heidelberg, Germany (1998).)

Identification and quantification of polycyclic aromatic hydrocarbon (PAH)-DNA adducts led to the discovery that there is a correlation between depurinating adducts and oncogenic mutations, suggesting that these adducts are the primary culprits in the tumor initiating pathway. This discovery was made by identifying the DNA adducts formed in mouse skin by dibenzo[a,l]pyrene (DB[a,l]P), 7,12-dimethylbenz[a]anthracene (DMBA) and benzo[a]pyrene (BP) and, at the same time, determining the mutations in the Harvey (H)-ras oncogene in mouse skin papillomas initiated by these three PAH (Table 1).

TABLE 1

Correlation of depurinating adducts with H-ras mutations in mouse skin papillomas

| PAH | Major DNA Adducts | H-ras Mutations | |
|---|---|---|---|
| | | No. of mutations/No. of mice | codon |
| DMBA | N7Ade (79%) | 4/4 CAA→CTA | 61 |
| DB[a,l]P | N7Ade (32%) | 10/12 CAA→CTA | 61 |
| | N3Ade (49%) | | |
| BP | C8Gua + N7Gua (46%) | 10/20 GGC→GTC | 13 |
| | N7Ade (25%) | 5/20 CAA→CTA | 61 |

These mutations correlate with the predominant formation of depurinating Ade adducts by DMBA and DP[a,l]P and the two-to-one ratio of depurinating Gua to Ade adducts formed by BP. This pattern of ras mutations suggests that the oncogenic mutations in mouse skin papillomas induced by these PAH are generated by misrepair of the apurinic sites derived from loss of the depurinating adducts. Because thousands of apurinic sites are formed by cells each day, repair of apurinic sites induced by PAH might be expected. The level of apurinic sites arising from treatment with PAH is, however, 15-120 times higher than those formed spontaneously, suggesting that this large increase in apurinic sites could lead to misrepair. In summary, apurinic sites can generate the mutations that play a critical role in the initiation of cancer, and formation of depurinating adducts has become the common denominator for recognizing the potential of a chemical to initiate cancer. (Cavalieri E. L. and Rogan E. G., Mechanisms of tumor initiation by polycyclic aromatic hydrocarbons in mammals. In: The Handbook of Environmental Chemistry: PAHs and Related Compounds, 3J, pp. 81-117, Neilson A. H. (ed.), Springer, Heidelberg, Germany (1998); Chakravarti D. et al., *Proc. Natl. Acad. Sci. USA*, 92, 10422-10426 (1995); Chakravarti D. et al., *Mutation Res.*, 456, 17-32 (2000); Lindahl T. and Nyberg B., *Biochemistry*, 11; 3610-3618 (1972); Chakravarti D. et al., *Oncogene*, 16, 3203-3210 (1998).)

Formation, Metabolism and DNA Adducts of Estrogens

Evidence that depurinating PAH-DNA adducts play a major role in tumor initiation provided the impetus for discovering the estrogen metabolites that form depurinating DNA adducts and can be potential endogenous initiators of cancer. Catechol estrogens (CE) are among the major metabolites of $E_1$ and $E_2$. If these metabolites are oxidized to the electrophilic CE quinones (CE-Q), they may react with DNA. Specifically, the carcinogenic 4-CE are oxidized to CE-3,4-Q, which react with DNA to form depurinating adducts. These adducts generate apurinic sites that may lead to oncogenic mutations, thereby initiating cancer. (Cavalieri E. L. and Rogan E. G., *Pharmacol. Ther.*, 55; 183-99 (1992); Cavalieri E. L. and Rogan E. G. Mechanisms of tumor initiation by polycyclic aromatic hydrocarbons in mammals. In: The Handbook of Environmental Chemistry: PAHs and Related Compounds, 3J, 81-117, Neilson A. H. (ed.), Springer, Heidelberg, Germany (1998); Chakravarti D. et al., *Proc. Natl. Acad. Sci. USA*, 92, 10422-10426 (1995); Cavalieri, et al., *Proc. Natl. Acad. Sci. USA*, 94, 10937-10942 (1997); Liehr J. G., et al., *J. Steroid Biochem.*, 24, 353-356 (1986); Li J. J. and Li S. A., *Fed. Proc.*, 46, 1858-1863 (1987); Newbold R. R. and Liehr J. G., *Cancer Res.*, 60, 235-237 (2000); Li K. M., et al., *Proc. Am. Assoc. Cancer Res.*, 39, 636 (1998); Chakravarti D., et al., *Mutation Res.*, 456, 17-32 (2000); Chakravarti D., et al., *Oncogene*, 16, 3203-3210 (1998); Chakravarti D., et al., *Oncogene*, 20, 7945-7953 (2001).)

Estrogen Metabolism.

Figure 2:
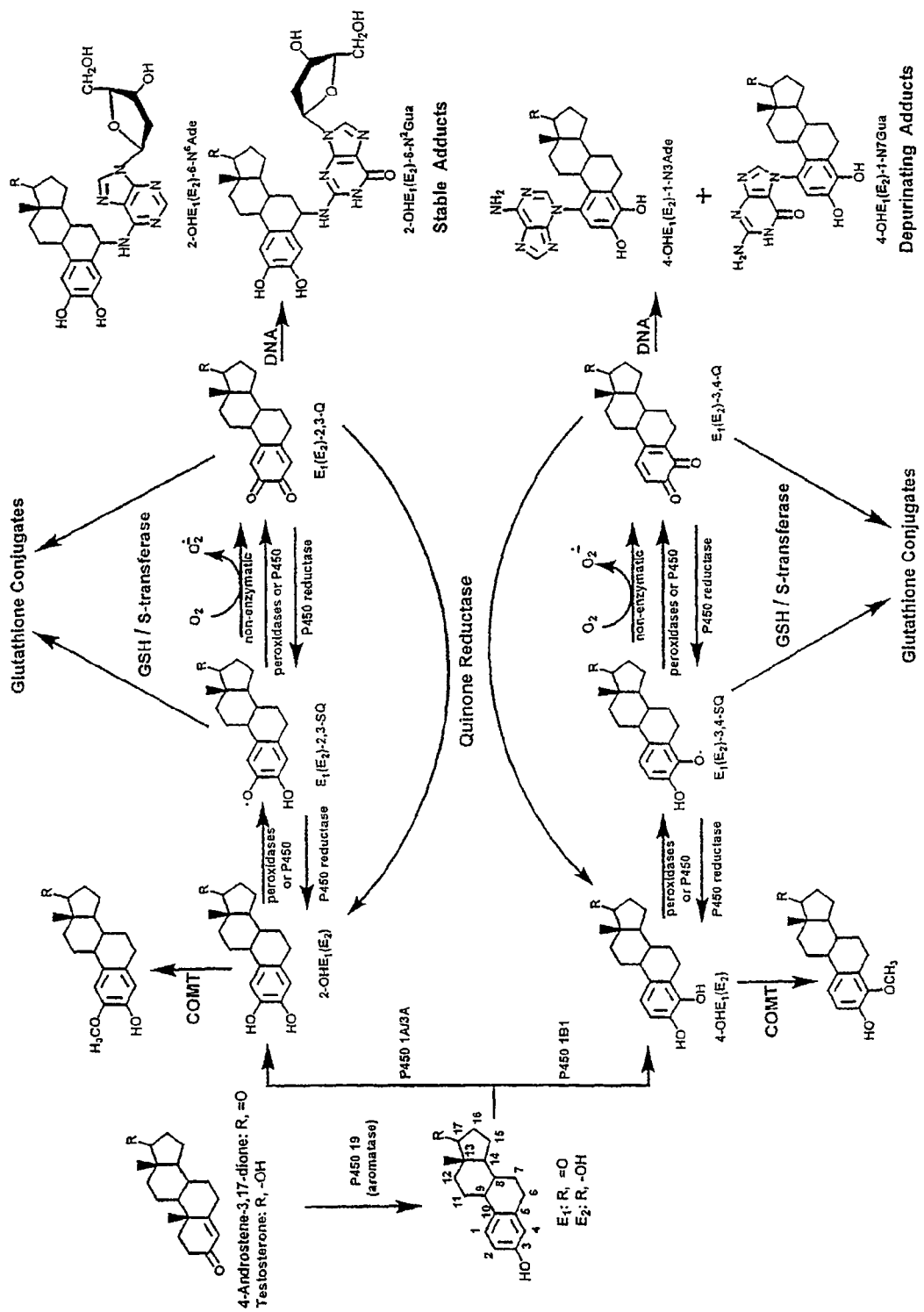
FIG. 2 depicts the formation, metabolism, conjugation and DNA adducts of estrogens.

$E_1$ and $E_2$ are obtained by aromatization of 4-androsten-3, 17-dione and testosterone, respectively, catalyzed by cytochrome P450 (CYP)19, aromatase (FIG. 2). The estrogens $E_1$ and $E_2$ are biochemically interconvertible by the enzyme 17β-estradiol dehydrogenase. $E_1$ and $E_2$ are metabolized via two major pathways: formation of CE and, to a lesser, extent, 16α-hydroxylation (not shown in FIG. 2). The CE formed are the 2- and 4-hydroxylated estrogens. The major 4-hydroxylase in extrahepatic tissues is CYP1B1. In general, the CE are inactivated by conjugating reactions such as glucuronidation and sulfation, especially in the liver (not shown in FIG. 2). The most common pathway of conjugation in extrahepatic tissues, however, occurs by O-methylation catalyzed by the ubiquitous catechol-O-methyltransferase (COMT). (Spink D. C., et al., *J. Steroid Biochem. Mol. Biol.*, 51, 251-258 (1994); Hayes C. L., et al., *Proc. Natl. Acad. Sci. USA*, 93, 9776-9781 (1996); Spink D. C., et al., *Carcinogenesis*, 19, 291-298 (1998); Mannisto P. T. and Kaakola S., *Pharmacol. Rev.*, 51, 593-628 (1999).)

A reaction that is competitive with the conjugation of CE is their catalytic oxidation to CE-semiquinones (CE-SQ) and CE-Q (FIG. 2). CE-SQ and CE-Q can be neutralized by conjugation with glutathione (GSH). A second inactivating pathway for CE-Q is their reduction to CE by quinone reductase and/or cytochrome P450 reductase. If these two inactivating processes are insufficient, CE-Q may react with DNA to form stable and depurinating adducts (FIG. 2). The carcinogenic 4-CE are oxidized to form predominantly the depurinating adducts 4-OHE$_1$(E$_2$)-1-N3Ade and 4-OHE$_1$(E$_2$)-1-N7Gua. Carcinogenic 2-CE are oxidized to form predominantly stable adducts, 2-OHE$_1$(E$_2$)-6-N$^6$dA and 2-OHE$_1$(E$_2$)-6-N$^2$dG, but also depurinating adducts to a much lesser extent. (DT Diaphorase A quinone reductase with special functions in cell metabolism and detoxification (Ernester L, Estabrook R W, Hochstein P, Orrenius S., Eds.) *Chemica Scripta* 27A (1987); Roy, D. and Liehr J. G., *J. Biol. Chem.*, 263, 3646-3651 (1988); Cavalieri E., et al., Estrogens as endogenous genotoxic agents: DNA adducts and mutations. In: JNCI Monograph 27: Estrogens as Endogenous Carcinogens in the Breast and Prostate, pp. 75-93, E. Cavalieri and E. Rogan (eds.), Oxford Press, Washington (2000); Liehr J. G., et al., *J. Steroid Biochem.*, 24, 353-356 (1986); Li J. J. and Li S., *Fed. Proc.*, 46, 1858-1863 (1987); Newbold R. R. and Liehr J. G., *Cancer Res.*, 60, 235-237 (2000); Cavalieri E. L., et al., *Proc. Natl. Acad. Sci. USA*, 94, 10937-10942 (1997); Li K. M., et al., *Proc. Am. Assoc. Cancer Res.*, 39, 636 (1998); Stack D. E., et al., *Chem. Res. Toxicol.*, 9, 851-859 (1996); Dwivedy I., et al., *Chem. Res. Toxicol.*, 5, 828-833 (1992); Van Aerden C., et al., *Analyst*, 123, 2677-2680 (1998).)

Redox Cycling of Catechol Estrogen Semiquinones and Quinones.

Figure 3:
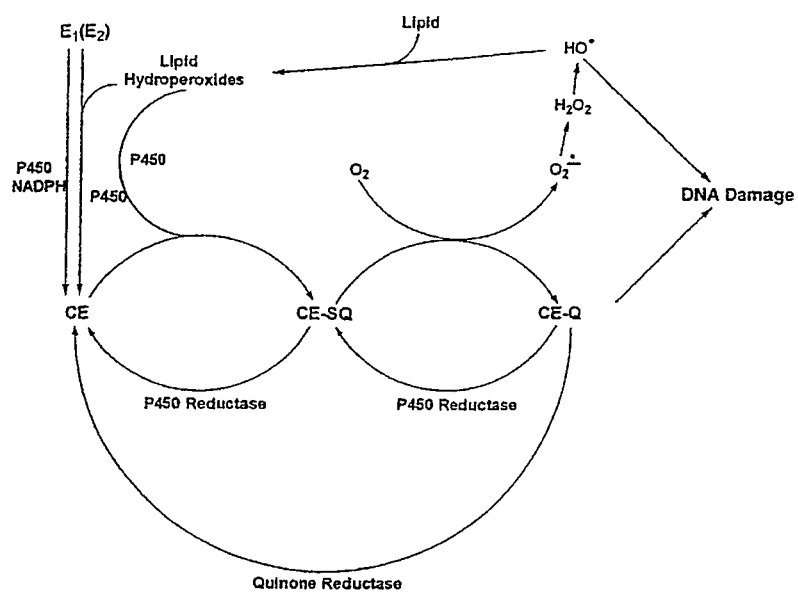
FIG. 3 demonstrates redox cycling of catechol estrogen semiquinones and quinones: DNA damage and formation of lipid hydroperoxides.

Redox cycling (FIGS. 2 and 3) generated by reduction of CE-Q to CE-SQ, catalyzed by cytochrome P450 reductase, and subsequent oxidation back to CE-Q by molecular oxygen forms superoxide anion radicals ($O_2^{\cdot -}$). These $O_2^{\cdot -}$ dismutate to $H_2O_2$, either spontaneously or, even faster, when the reaction is catalyzed by superoxide dismutase. $H_2O_2$ is rather nonreactive, except in the presence of reduced transition metal ions, namely $Fe^{2+}$ and $Cu^+$, which cause formation of indiscriminate oxidants, the hydroxyl radicals. These reactive species can damage DNA by formation of oxygenated bases. Concurrently, hydroxyl radicals can initiate the lipid peroxidation process, generating lipid hydroperoxides that can serve as unregulated cofactors for oxidation of CE by cytochrome P450. In contrast, under normal conditions nicotinamide dinucleotide phosphate NADPH serves not only as a cofactor, but also regulates cytochrome P450 in the oxidation of CE. Thus, once lipid hydroperoxides are formed, the oxidation of CE to CE-SQ and CE-Q can become a self-generating process that unbalances estrogen homeostasis and leads to formation of CE-Q. (Liehr J. G. and Roy D., *Free Radical Biol. Med.,* 8, 415-423 (1990); Nutter L. M., et al., *Chem. Res. Toxicol.,* 7, 23-28 (1994); Malins D. C., et al., *Cancer,* 17, 3036-3043 (1993); Lavigne J. A., et al., *Cancer Res.,* 61, 7488-7494 (2001); Kappus H., Lipid peroxidation: Mechanisms, analysis, enzymology and biological relevance. In: Sies, H., ed., Oxidative Stress, New York, Academic Press, 273-310 (1985).)

Binding of Catechol Estrogen Quinones to DNA.

To determine whether DNA adducts are formed in biological systems, $E_2$-3,4-Q or enzymatically-activated 4-hydroxyestradiol (4-$OHE_2$) was reacted with DNA for 2 h at 37° C. The stable adducts were quantified by the $^{32}$P-postlabeling method, and the depurinating adducts were analyzed by high pressure liquid chromatography (HPLC) interfaced with an electrochemical detector. When $E_2$-3,4-Q reacted with DNA, almost the same amount of the depurinating adducts 4-$OHE_2$-1-N3Ade and 4-$OHE_2$-1-N7Gua were obtained, and the amount of stable adducts was 0.02% of the depurinating ones. Activation of 4-$OHE_2$ by horseradish peroxidase gave similar results, whereas the mammalian lactoperoxidase produced a similar amount of N3Ade adduct, but about 50% more N7Gua adduct. The same two depurinating adducts were obtained in equal but smaller amounts when 4-$OHE_2$ was activated with tyrosinase or phenobarbital-induced rat liver microsomes. In all cases, the level of stable adducts was 0.02% or less compared to the depurinating adducts (Li K. M., et al., *Proc. Am. Assoc. Cancer Res.,* 39, 636 (1998); Cavalieri, et al., unpublished results).

DNA adducts were analyzed in vivo in rat mammary gland and mouse skin after treatment of the animals with $E_2$-3,4-Q or 4-$OHE_2$. Female ACI rats, which are susceptible to $E_2$-induced mammary tumors, were treated by intramammillary injection of $E_2$-3,4-Q or 4-$OHE_2$ (200 nmol in 20 μL DMSO/gland at four teats) for 1 h. The mammary tissue was excised, extracted and analyzed for stable and depurinating adducts. N3Ade and N7Gua adducts from both 4-$OHE_2$ and 4-$OHE_1$ were detected in the range of 100-300 μmol/mol DNA-P. The level of stable adducts was not above the low level detected in untreated mammary tissue. Similarly, female SENCAR mice were treated topically on a shaved area of dorsal skin with $E_2$-3,4-Q [200 nmol in 50 μL acetone/DMSO (9:1)] for 1 h. The treated area of skin was excised, extracted and analyzed for stable and depurinating adducts. Equal amounts of 4-$OHE_2$-1-N3Ade and 4-$OHE_2$-1-N7Gua, approximately 12 μmol/mol DNA-P, were detected, and the amount of stable adducts was 0.02% of the depurinating adducts. These results in rats and mice demonstrate that the depurinating CE-DNA adducts are formed in vivo, generating apurinic sites in the DNA that could lead to oncogenic mutations. (Shull J. D., et al., *Carcinogenesis,* 18, 1595-1601 (1997); Cavalieri, et al., unpublished results; Chakravarti D., et al., *Oncogene,* 20, 7945-7953 (2001).)

Depurinating Adducts and Induction of Mutations

Mouse skin provides a model system to study the conversion of DNA lesions, such as carcinogen-induced depurinating and stable DNA adducts, into mutations. In mouse skin, tumor initiation occurs when these DNA lesions are converted into oncogenic mutations in the H-ras gene. Previous studies indicated that stable adducts are inefficiently removed by excision repair, and cells containing these adducts enter the S-phase. In the S-phase, occasional mutations are induced when replicative DNA polymerases go over adducted templates. Therefore, it was concluded that adduct-induced mutagenesis occurs in proliferating cells. These studies, however, did not address the fate of apurinic sites formed by the depurinating adducts. (Maher V. M., and McCormick J. J., Role of DNA lesions and repair in the transformation of human cells. In: D. Grunberger, S. P. Groff (eds) Mechanisms of Cellular Transformation by Carcinogenic Agents. Pergamon Press, New York, 135-149 (1987); Kaufman W. K., *Cancer Metastasis Rev,* 14, 31-41 (1995); Moriya M., et al., *Biochemistry,* 35, 16646-16651 (1996).)

Resting Cells are Greatly Susceptible to Tumor Formation.

Mouse skin is most susceptible to tumor formation by carcinogens during the telogen phase of the hair cycle. At telogen, epidermal thickness is low, indicating that at these times epidermal cells are in the resting phase. DMBA, which forms 99% depurinating adducts and 1% stable adducts, induces several-fold more tumors when applied to resting phase skin. This suggests that apurinic sites induced by the depurinating DNA adducts may be most efficiently converted into oncogene-activating mutations in G0-G1 phase cells. These questions were examined with DB[a,l]P, the strongest among PAH carcinogens, which also forms 99% depurinating adducts and 1% stable adducts in mouse skin DNA and induces the H-ras codon 61 (CAA to CTA) mutation in tumors. (Devanesan P. D., et al., *Chem. Res. Toxicol.,* 6, 364-371 (1993); Andreasen E., *Acta. Pathol. Scand.,* 32, 157-164 (1953); Cavalieri E. L. and Rogan E. G., Mechanisms of tumor initiation by polycyclic aromatic hydrocarbons in mammals. In: The Handbook of Environmental Chemistry: PAHs and Related Compounds, 3*J,* 81-117, Neilson A. H. (ed.), Springer, Heidelberg, Germany (1988); Chakravarti D., et al., *Proc. Natl. Acad. Sci. USA,* 92, 10422-10426 (1995).)

Using a polymerase chain reaction-restriction fragment length polymorphism (PCR-RFLP) technique, it was found that treatment of mouse skin with 200 nmol of DB[a,l]P resulted in the induction of these codon 61 mutations as early as one day after treatment. In this technique, a segment of the H-ras gene is PCR-amplified and the product is restricted with XbaI to examine the induction of a RFLP from the codon 61 mutation. It was observed that at one day, 0.1% of the H-ras genes in the treated area of skin contained the codon 61 mutation, and then the population of these mutations increased to a maximum of 5% between 3 and 4 days after DB[a,l]P treatment. Subsequently, the level of mutations was reduced to background levels (0.0001%). The early time of induction of the codon 61 mutations (one day after DB[a,l]P treatment) coincides with suppression of DNA synthesis and induction of excision repair. Therefore, perhaps DB[a,l]P-induced DNA damage is converted into mutations by error-prone excision repair in pre-S-phase cells. (Chakravarti D., et al., *Oncogene*, 16, 3203-3210 (1998); Slaga T. J., et al., *Cancer Res.*, 34a, 771-777 (1974); Sawyer T. W., et al., *Carcinogenesis*, 9, 1197-1202 (1988); Gill R. D., et al., *Environ. Mol. Mutagen.*, 18, 200-206 (1991).)

Error-Prone Repair of Apurinic Sites is a Mechanism of Tumor Initiation.

Figure 4:
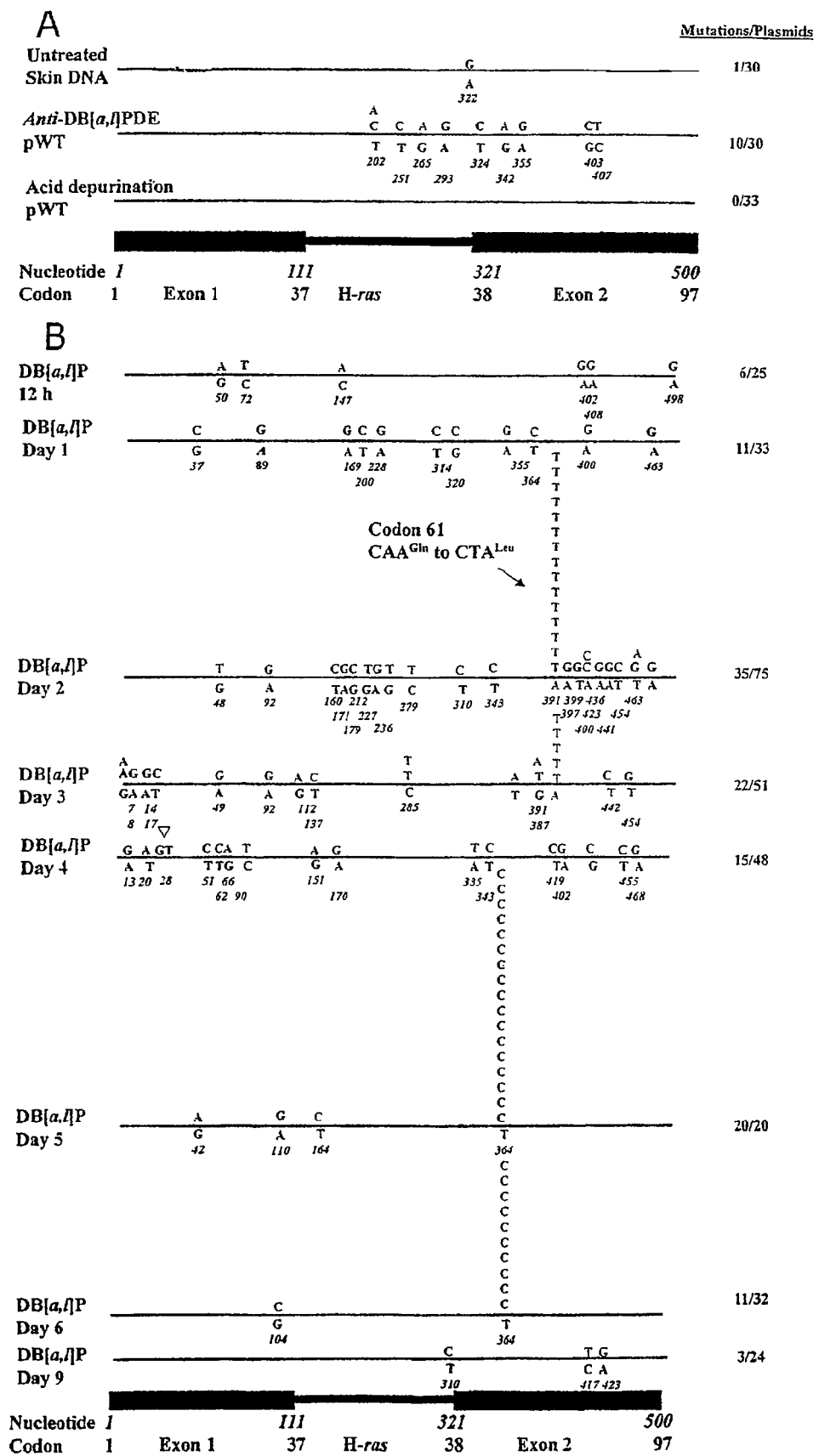
FIGS. 4A-D depict H-ras mutations induced by DB[a,l]P or its metabolite, anti-DB[a/l]PDE. Wild type sequences and nucleotide numbers (GenBank accession No. U89950) are indicated below and mutations are indicated above the line. (A) PCR artifact mutations induced in untreated skin DNA and in a cloned H-ras gene (pWT) treated with anti-DB[a,l] PDE or with acid. Under the treatment conditions, anti-DB [a,l]PDE induces 1 adduct per 1000 bases and acid induces 1 depurination per 170 bases (Chakravarti, D. Et al., *Mutat. Res.*, 456, 17-32 (2000)). (B) H-ras mutations in mouse skin DNA after treatment with 200 nmol DB[a,l]P in 100 μL acetone. At 12 h-1 d, the spectra contained mostly A/T to G/C mutations. At days 2 and 3, multiple codon 61 mutations were observed. At 4 d, no clear pattern of mutations could be determined. At days 5 and 6, multiple codon 52 (CTA to CCA) mutations were observed. Few mutations were observed at day 9. ∇, insertion. (C) H-ras mutations in mouse skin DNA after treatment with 200 nmol of anti-DB[a,l]PDE in 100 μL acetone. Fifty to sixty percent of mutations between days 1 to 4 were A/T to G/C mutations. (D) H-ras mutations after TDG treatment of DNA from anti-DB[a,l]PDE-treated pWT and from DB[a,l]P- or anti-DB[a,l]PDE-treated mouse skin. TDG treatment resulted in drastic reduction of A/T to G/C mutations and the observation of multiple codon 61 (CAA to CTA) mutations at day 1. These mutations were also observed at days 2 and 3. In addition, at days 2 and 3, multiple codon 13 (GGC to GTC) mutations were observed.

Evidence in support of this was obtained from a comparative study of mutations in the mouse skin H-ras gene induced by 200 nmol of DB[a,l]P or 200 nmol of anti-DB[a,l]P-11, 12-dihydrodiol-13,14-epoxide (anti-DB[a,l]PDE). Unlike DB[a,l]P, anti-DB[a,l]PDE forms 97% stable adducts and 3% depurinating adducts in DNA. In these experiments, the types of mutations that are induced in the early preneoplastic times was identified (12 h to 9 days after treatment) and then analyzed whether these mutations were induced as a result of error-prone repair (FIG. 4). The mutations were identified by PCR amplifying a segment of the H-ras gene from DNA extracted from mouse skin treated with one of the carcinogens, cloning the PCR products in a plasmid, isolating individual subclones and sequencing the H-ras inserts to identify mutations. (Chakravarti D., et al., *Mutation Res.*, 456, 17-32 (2000); Cavalieri E. L. and Rogan E. G., Mechanisms of tumor initiation by polycyclic aromatic hydrocarbons in mammals. In: The Handbook of Environmental Chemistry: PAHs and Related Compounds, 3*J*, 81-117, Neilson A. H. (ed.), Springer, Heidelberg, Germany (1998).)

Figure 5:
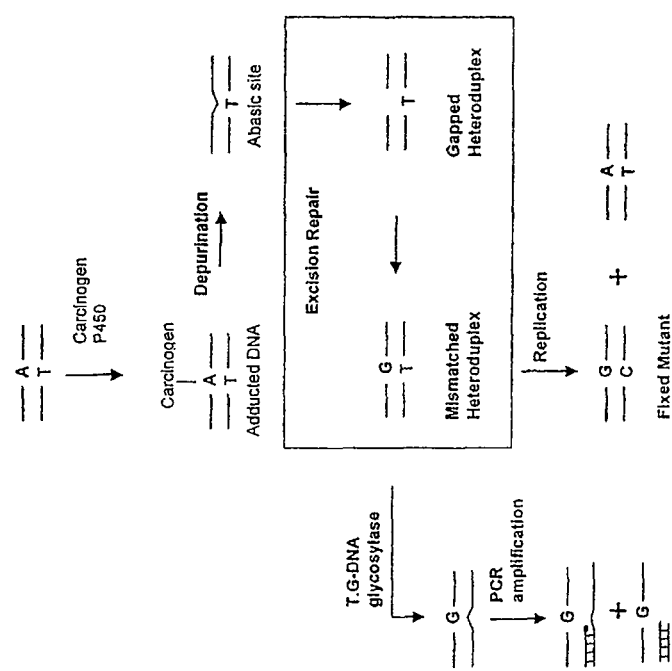
FIG. 5 depicts a proposed pathway of formation of A to G mutations by error-prone base excision repair of carcinogen-induced apurinic sites and the detection of the resulting G.T heteroduplexes by the TDG-PCR technique. The conversion of G.T heteroduplexes into G. apyrimidinic sites results in a drastic reduction in the formation of A/T to G/C mutations. G.T heteroduplexes are converted into fixed mutations (G.C and A.T pairs) by one round of replication.

The mutation spectra induced by DB[a,l]P contained 90% A/T to G/C mutations at day 1. This correlated with the abundant DB[a,l]P-Ade depurinating adducts (81% of total adducts) and suggested that these A/T to G/C mutations were induced at Ade depurinations. Thus, the adducts could be correlated with these early preneoplastic mutations, as well as with the clonal H-ras mutations found in the tumors (Table 1). If Ade depurinations induce these A/T to G/C mutations, they may be A to G mutations generated as G.T heteroduplexes by error-prone excision repair (FIG. 5).

Using a novel technique, it was determined that these A to G mutations in the H-ras gene are initially induced as G.T heteroduplexes. In this technique, G.T heteroduplexes in skin DNA are converted to G.apyrimidinic sites by treatment with T.G-DNA glycosylase (TDG) (FIG. 5). (Chakravarti D., et al., *Mutation Res.*, 456, 17-32 (2000).)

Depurinated DNA templates are refractory to PCR amplification. To demonstrate this point, a mixture of two plasmids (one contained the wild type H-ras exon 1-2 segment (pWT) and the other contained the same DNA with the codon 61 (CAA to CTA) mutation (pMUTX)) was PCR amplified. The yield of pMUTX in the PCR product was determined by XbaI digestion. When pMUTX was incubated in an acidic buffer to induce a relatively small amount of depurination that did not significantly degrade the plasmid (~1 depurination/H-ras segment), mixed with untreated pWT and PCR amplified, a drastically reduced amount of the product was XbaI-digestible. This confirmed that depurinated templates are refractory to PCR amplification. Failure to score mutations in pWT depurinated either by acid-treatment (FIG. 4A) or through depurinating adduct formation by $E_2$-3,4-Q (FIG. 7A) may be related to the unavailability of depurinated templates for PCR amplification. (Chakravarti D., et al., *Mutation Res.*, 456, 17-32 (2000); Fromenty B., et al., *Nucl. Acids Res.*, 28, e50 (2000).)

Since abasic site-containing DNA molecules are refractory to PCR amplification, the conversion of G.T heteroduplexes into G. apyrimidinic sites makes H-ras molecules containing these heteroduplexes unamplifiable. Under these circumstances, PCR preferentially amplifies templates that do not contain G.T heteroduplexes. As a result, PCR amplification of the H-ras gene from TDG-treated skin DNA, followed by cloning the PCR product and isolating and determining the sequence of individual subclones, causes a specific, drastic reduction of A to G mutations in the mutation spectra. In addition, the preferential PCR amplification artificially enriches low-abundance mutations that are observed only in TDG-treated spectra.

Following the entry of skin cells into S-phase, however, the G.T heteroduplexes are converted into G.C and A.T base pairs by one round of replication. At this stage, TDG treatment does not reduce the frequency of A to G mutations in the spectra. Thus, the specific reduction of A to G mutations in the mutation spectra by the TDG-PCR procedure characterizes these mutations as G.T heteroduplexes. The TDG-PCR procedure resulted in a drastic reduction in the population of A/T to G/C mutations on day 1, but did not make a significant change at days 2 and 3 (Table 2). Therefore, A to G mutations remained as G.T heteroduplexes until one day after DB[a,l]P treatment of the skin; beyond which they were present as G.C and A.T mutations, presumably by replication. Flow cytometric analysis of epidermal keratinocytes isolated from DB[a,l]P-treated mouse skin confirms that cells begin to enter the S-phase one day after the treatment. (Chakravarti D., et al., *Mutation Res.*, 456, 17-32 (2000); Chakravarti et al., unpublished results).

A major difference in mutation spectra induced by DB[a,l]P and anti-DB[a,l]PDE was the presence or absence of multiple codon 61 (CAA to CTA) mutations in early preneoplastic skin. These mutations were detectable one day after DB[a,l]P treatment by the PCR-RFLP procedure, which indicated that they constitute 0.1% of H-ras genes, and in the mutation spectrum obtained after TDG treatment of skin DNA. Since these CAA to CTA mutations were observed during the active repair period, it was hypothesized that they were also induced by error-prone repair as T.T heteroduplexes. Since these mutations were present in days 2-3 in a significantly greater frequency relative to other mutations in the spectra, it was hypothesized that the increase in frequency was due to a clonal proliferation of codon 61-mutated (initiated) cells. Further studies suggest that at days 2-3, these codon 61-mutated cells express activated Ras protein (Chakravarti D., et al., *Oncogene*, 16, 3203-3210 (1998); Chakravarti D., et al., *Mutation Res.*, 456, 17-32 (2000); Chakravarti et al., unpublished observations).

On the other hand, anti-DB[a,l]PDE formed approximately 50% A/T to G/C mutations, which correlated with 48.5% formation of anti-DB[a,l]PDE-Ade stable adducts in mouse skin DNA (Table 2). The frequency of these mutations was not significantly reduced by the TDG-PCR procedure, indicating that these mutations were not induced by error-prone repair. Studies conducted in other laboratories also indicate that nucleotide excision repair of bulky stable adducts is error-free. When the pWT plasmid was treated with anti-DB[a,l]PDE in vitro (97% bulky stable adducts) and subjected to PCR amplification, A/T to G/C mutations was also found to constitute 50% of all mutations (5 out of 10) (FIG. 4A). These mutations are induced by translesional synthesis over bulky stable adducts by the PCR polymerases. If, as has been proposed by others, only a small population of PAH-induced bulky stable adducts is removed by pre-replication repair, a large fraction of anti-DB[a,l]PDE-induced adducts would persist in the mouse skin DNA. It is, therefore, possible that the mutations found in anti-DB[a,l]PDE-treated mouse skin DNA are adduct-induced PCR artifacts. The similarity of the frequencies of A/T to G/C mutations in vitro and in skin is consistent with this idea.

TABLE 2

The frequency of changes in DB[a, l]P-induced A/T to G/C mutations by TDG treatment followed by PCR

| PAH | DNA | Day | A/T to B/C mutations/total mutations | |
|---|---|---|---|---|
| | | | −TDG | +TDG |
| anti-DB[a, l]PDE | pWT | — | 5/10 (50%) | 3/5 (60%) |
| | skin | 1 | 5/8 (62.5%) | 4/5 (80%) |
| DB[a, l]P | skin | 1 | 10/11 (90%) | 2/10 (20%) |
| | | 2 | 11/35 (31%) | 6/22 (27%) |
| | | 3 | 7/22 (31%) | 8/25 (32%) |

(Watanabe M., et al., *Mutat Res.*, 146, 285-294 (1985); Maher V. M. and McCormick J. J., Role of DNA lesions and repair in the transformation of human cells. In: D. Grunberger, S. P. Groff (eds) Mechanisms of Cellular Transformation by Carcinogenic Agents. Pergamon Press, New York, pp. 135-149 (1987).)

Four days after treating mouse skin with DB[a,l]P, no codon 61 mutations were observed in 48 plasmids that contained 15 other mutations (FIG. 4B). No definite patterns of mutations were recognized at this time. At days 5 and 6, the mutation spectra were mainly limited to codon 52 (CTA to CCA) mutations. This coincided with the early phase of DB[a,l]P-induced hyperplasia that starts at day 5 and persists beyond day 10. The codon 52 mutation may be oncogenic, but further study is required. (Casale, G. P., et al., *Fund. Appl. Tox.*, 36, 71-78 (1997); Casale, G. P., et al., *Mol. Car.*, 27, 125-140 (2000).)

The repair error-induced A/T to G/C mutations in DB[a,l] P-treated mouse skin frequently occurred 3' to a sequence element, TGN-doublet (FIG. 6), whereas these mutations in anti-DB[a,l]PDE-treated skin did not show a sequence context preference (not shown in FIG. 6). This suggests that the sequence context of the depurinated base may determine the erroneous base incorporated by repair. It is also noted that DB[a,l]P induces approximately 120-fold more depurinations through the depurinating adducts than are formed by spontaneous base loss (10,000-20,000 depurinations/cell/day). This raised the possibility that abundant depurination may be a factor in inducing infidelity in repair. (Chakravarti D., et al., *Mutation Res.*, 45, 17-32 (2000); Cavalieri E. L. and Rogan E. G., Mechanisms of tumor initiation by polycyclic aromatic hydrocarbons in mammals. In: The Handbook of Environmental Chemistry: PAHs and Related Compounds, 3J, 81-117, Neilson A. H. (ed.), Springer, Heidelberg, Germany (1998); Chakravarti D., et al., *Proc. Natl. Acad. Sci. USA*, 92, 10422-10426 (1995); Lindahl T. and Nyberg B., *Biochemistry*, 11, 3610-3618 (1972); Lindahl T. *Nature*, 362, 709-715 (1993).)

Effect of a Burst of DNA Depurination.

Treatment of mouse skin with $E_2$-3,4-Q provided evidence that abundant depurination may induce errors in repair. Like DB[a,l]P, $E_2$-3,4-Q forms predominantly depurinating adducts in mouse skin DNA, consisting of roughly equal amounts of two depurinating adducts (4-OHE$_2$-1-N3Ade and 4-OHE$_2$-1-N7Gua). The N3Ade adduct depurinates instantaneously after its formation, whereas the N7Gua adduct depurinates slowly, with a half-life of 5 h. The difference in the rate of depurination of the two adducts provided a way to examine the effect of abundant depurination on repair fidelity. Briefly, $E_2$-3,4-Q would challenge the mouse skin repair machinery with a burst of Ade-specific depurination and slow-release Gua-specific depurination. Should a burst of depurination be a contributing factor in causing repair to be error-prone, a greater frequency of Ade-specific mutations compared to Gua-specific mutations would be expected in the mouse skin DNA. (Chakravarti D., et al., *Oncogene*, 20, 7945-7953 (2001); Li K.-M., et al., *Proc. Am. Assoc. Cancer Res.*, 40, 46 (1999).)

Figure 7:
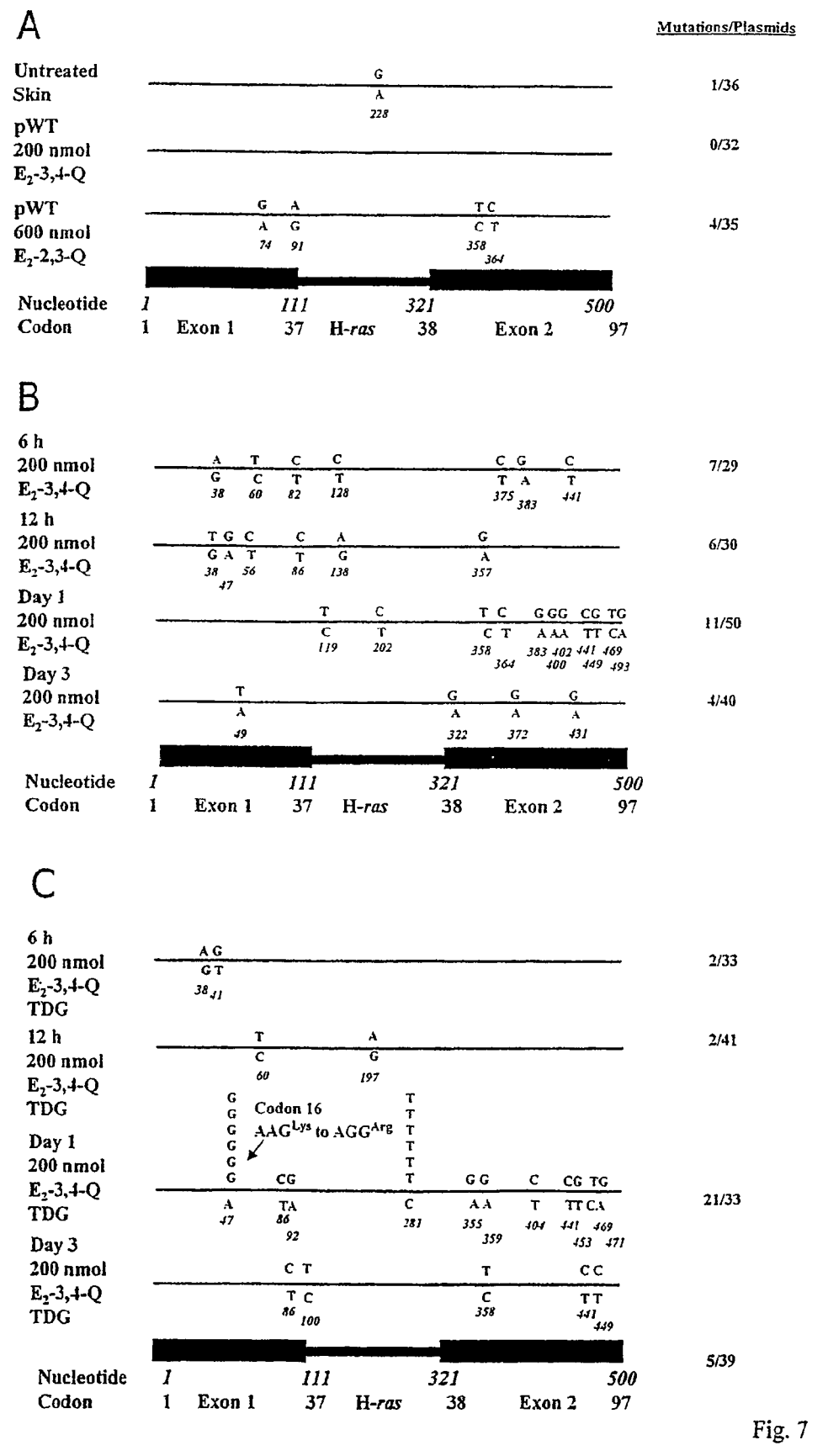

Treatment of mouse skin with 200 nmol of $E_2$-3,4-Q induced primarily A/T to G/C mutations in the H-ras gene (FIG. 7). For example, 6 h after $E_2$-3,4-Q treatment, 7 mutations were identified among 29 H-ras inserts. Five of the seven were A/T to G/C mutations. At 12 h, four out of the six mutations found in 30 H-ras inserts were A/T to G/C mutations. At day 1, seven out of the 11 mutations found among 50 plasmids were A/T to G/C mutations. Cells do not have enough time to replicate by 6 h, but they may undergo repair. The observation that $E_2$-3,4-Q induces mutations at 6 h is, therefore, a basis to propose that these mutations are induced by error-prone repair. To confirm this, TDG-PCR analysis of these mutations was conducted (FIG. 7). Specifically, at 6 h, TDG treatment reduced the frequency of the A/T to G/C mutations from 5 in 29 H-ras inserts to 0 in 33 H-ras inserts. At 12 h, the change was from 4 in 30 H-ras inserts to 0 in 41 plasmids. These results suggest that at 6-12 h, A/T to G/C mutations were in the form of G.T heteroduplexes. By day 1, a major change in the frequency of A/T to G/C mutations was not observed, following TDG treatment, suggesting that G.T heteroduplexes were present as G.C and A.T pairs. The TDG-treated 1 day spectrum was dominated by two clonal mutations of equal frequency (codon 16 AAG to AGG and intronic C to T mutations). Because it is unlikely that the intronic mutation would affect Ras activity and the two clonal mutations were found in the same frequency, these mutations may be allelic, belonging to a clonally proliferating population. In contrast, TDG treatment of day 3 DNA did not make any perceptible changes from the TDG-untreated spectrum. This suggests that the mutations found at day 3 were double-stranded and could not be affected by TDG treatment. (Chakravarti D., et al., *Oncogene*, 20, 7945-7953 (2001).)

$E_2$-3,4-Q-induced early A/T to G/C mutations were frequently found at Ade depurinations 5' to G residues. This supports the hypothesis that the sequence context of depurination influences the selection of which base is incorporated during error-prone repair.

Although these studies suggest that depurinating adducts play a major role in inducing transforming mutations to begin the process of tumorigenesis, the stable adducts can also contribute to these processes. Studies indicate that erroneous base incorporation during replication over various bulky stable adducts contributes to the induction of transforming mutations. For example, the BP-7,8-dihydrodiol-9, 10-epoxide-$N^2$dG stable adduct induces A incorporation, forming G to T mutations and the corresponding $N^6$dA stable adduct induces C incorporation, forming A to G mutations. Similar studies indicate that $E_2$-2,3-Q, which induces primarily bulky stable adducts, is also mutagenic. The 2-OHE$_2$-$N^6$dA stable adducts cause mostly A to T mutations and some A to G mutations, whereas 2-OHE$_2$-$N^2$dG stable adducts cause mainly G to T mutations. (Moriya M., et al., *Biochemistry*, 35, 16646-16651 (1996); Chary P., et al., *J. Biol. Chem.*, 270, 4990-5000 (1995); Stack D. E., et al., *Chem. Res. Toxicol.*, 9, 851-859 (1996); Dwivedy I., et al., *Chem. Res. Toxicol.*, 5, 828-833 (1992); Van Aerden C., et al., *Analyst*, 123, 2677-2680 (1998); Terashima I., et al., *Biochemistry*, 37, 8803-8807 (1998); Terashima I., et al., *Biochemistry*, 37: 13807-13815 (1998); Terashima I., et al., *Biochemistry*, 40: 8-14 (2001).)

Estrogen Homeostasis

There are several factors that unbalance estrogen homeostasis, namely, the equilibrium between activating and deactivating metabolic pathways with the scope of averting the reaction of endogenous CE-Q with DNA (FIG. 2). The first critical factor could be excessive synthesis of $E_2$ by overexpression of aromatase, CYP19, in target tissues and/or the presence of excess sulfatase that converts stored $E_1$ sulfate to $E_1$. The observation that breast tissue can synthesize $E_2$ in situ suggests that much more $E_2$ is present in some sites of target tissues than would be predicted from plasma concentrations. (Miller W. R. and O'Neill J., *Steroids*, 50, 537-548 (1987); Simpson E. R., et al., *Endocrine Rev.*, 15, 342-355 (1994); Yue W., et al., *Cancer Res.*, 58, 927-932 (1998); Yue W., et al., *Cancer*, 6, 157-164 (1999); Jefcoate C. R., et al., Tissue-specific synthesis and oxidative metabolism of estrogens. In: JNCI Monograph 27: Estrogens as Endogenous Carcinogens in the Breast and Prostate, pp. 95-112, Cavalieri E. and Rogan E. (eds.), Oxford Press, Washington (2000); Reed M. J. and Purohit A. *Endocrine Review*, 18, 701-715 (1997).)

A second critical factor in unbalancing estrogen homeostasis might be the presence of high levels of 4-CE due to overexpression of CYP1B1, which converts $E_2$ predominantly to 4-$OHE_2$ (FIG. 2). A relatively large amount of 4-CE could lead to more extensive oxidation to CE-3,4-Q, with increased likelihood of damaging DNA. (Spink D. C., et al., *J. Steroid Biochem. Mol. Biol.*, 51, 251-258 (1994); Hayes C. L., et al., *Proc. Natl. Acad. Sci. USA*, 93, 9776-9781 (1996); Spink D. C., et al., *Carcinogenesis*, 19, 291-298 (1998).)

A third factor could be a lack or low level of COMT activity. If this enzyme is insufficient, either through a low level of expression or its low activity allele, 4-CE will not be effectively methylated, facilitating their oxidation to the ultimate carcinogenic metabolites CE-3,4-Q (FIG. 2).

Studies in Syrian Golden Hamsters.

The hamster provides an excellent model for studying activation and deactivation (protection) of estrogen metabolites in relation to formation of CE-Q. In fact, implantation of $E_1$ or $E_2$ in male Syrian golden hamsters induces renal carcinomas in 100% of the animals, but does not induce liver tumors. Therefore, comparison of the profiles of estrogen metabolites, conjugates and DNA adducts in the two organs should provide information concerning the imbalance in estrogen homeostasis generated by treatment with $E_2$. Hamsters were injected with 8 µmol of $E_2$ per 100 g body weight, and liver and kidney extracts were analyzed for 31 estrogen metabolites, conjugates and depurinating DNA adducts by HPLC interfaced with an electrochemical detector. Neither the liver nor the kidney contained 4-methoxyCE, presumably due to the known inhibition of COMT by 2-CE. More O-methylation of 2-CE was observed in the liver, whereas more formation of CE-Q was detected in the kidney (Table 3). (Li, J. J., et al., *Cancer Res.*, 43, 5200-5204 (1983); Cavalieri E. L., et al., *Chem. Res. Toxicol.*, 14, 1041-1050 (2001); Roy D., et al., *Carcinogenesis*, 11, 459-462 (1990).)

These results suggest less protective methylation of 2-CE and more pronounced oxidation of CE to CE-Q in the kidney. To further investigate the rationale behind this interpretation, hamsters were first pretreated with L-buthionine (SR)-sulfoximine, an inhibitor of GSH synthesis, to deplete GSH levels. The hamsters were then treated with $E_2$. Very low levels of CE and methoxyCE were observed in the kidney compared to the liver, suggesting little protective reduction of CE-Q to CE in the kidney (Table 3). Most significantly, the 4-$OHE_1(E_2)$-1-N7Gua depurinating adduct, arising from reaction of CE-3,4-Q with DNA, was detected in the kidney, but not in the liver (Table 3). From these results, it seems that tumor initiation in the kidney occurs because of poor methylation of CE, which favors the competitive oxidation of CE to CE-Q, and poor reductase activity to remove CE-Q. Thus, these two effects lead to a large amount of CE-Q, which can react with biological nucleophiles, including those in DNA. (Cavalieri E. L., et al., *Chem. Res. Toxicol.*, 14, 1041-1050 (2001).)

TABLE 3

Selected estrogen metabolites, conjugates and adducts formed in hamsters treated with $E_2$ or $E_2$ plus BSO[a]

| Metabolites/ | nmol/g tissue | | | |
| | Kidney | | Liver | |
| conjugates[b]/adducts | $E_2$ | $E_2$ + BSO | $E_2$ | $E_2$ + BSO |
|---|---|---|---|---|
| 2-$OHE_1(E_2)$ | 2.66 | 1.02 | 4.75 | 10.27 |
| 4-$OHE_1(E_2)$ | 0.29 | 0.14 | 0.44 | 1.04 |
| 2-$OCH_3E_1(E_2)$ | 1.13 | 0.42 | 4.16 | 4.46 |
| $E_1(E_2)$-2,3-Q conjugates[b] | 1.36 | 0.21 | 0.63 | 0.13 |
| $E_1(E_2)$-3,4-Q conjugates[b] | 0.30 | 0.09 | 0.06 | 0.01 |
| $E_1(E_2)$-3,4-Q N7Gua adducts | <0.01 | 0.27 | <0.01 | <0.01 |

[a]Data are from Cavalieri et al., Chem Res. Toxicol., 14: 10-41 (2001). BSO: L-buthionine (SR)-sulfoximine. The notation $E_1(E_2)$ indicates that the metabolites, conjugates or adducts of both $E_1$ and $E_2$ are detected.
[b]Conjugates include all compounds produced by reaction of CE-Q with GSH and detected as GSH, cysteine or N-acetylcysteine conjugates.

Studies in Estrogen Receptor-α Knockout (ERKO)/Wnt-1 Mice.

A novel model for breast cancer was established by crossing mice carrying the Wnt-1 transgene (100% of adult females develop spontaneous mammary tumors) with the ERKO mouse line, in which the mice lack estrogen receptor-α and estrogen receptor-β is not detected in the mammary tissue. Mammary tumors develop in these mice despite the lack of functional estrogen receptor-α. To begin investigating whether estrogen metabolite-mediated genotoxicity may play an important role in the initiation of mammary tumors, the pattern of estrogen metabolites and conjugates was analyzed in ERKO/Wnt-1 mice. Extracts of hyperplastic mammary tissue and mammary tumors were analyzed by HPLC interfaced with an electrochemical detector. Picomole amounts of the 4-CE were detected, but their methoxy conjugates were not. Neither the 2-CE nor 2-methoxyCE were detected. 4-CE-GSH conjugates or their hydrolytic products (conjugates of cysteine and N-acetylcysteine) were detected in picomole amounts in both tumors and hyperplastic mammary tissue, demonstrating the formation of CE-3,4-Q. These preliminary findings indicate that estrogen homeostasis is unbalanced in the mammary tissue, in that the normally minor 4-CE metabolites were detected in the mammary tissue, but not the normally predominant 2-CE. In addition, methylation of CE was not detected, whereas formation of 4-CE-GSH conjugates was. (Bocchinfuso W. P., et al., *Cancer Res.*, 59, 1869-1876 (1999); Devanesan P, et al., *Carcinogenesis*, 22, 1573-1576 (2001).)

Studies in Human Breast Tissue Specimens.

Imbalances in estrogen homeostasis were also observed in women with breast carcinoma compared to women without breast cancer (Table 4). Breast tissue specimens obtained from women undergoing breast biopsy or surgery were analyzed for 31 estrogen metabolites, conjugates and depurinating DNA adducts by HPLC with electrochemical detection. In women without breast cancer, a larger amount of 2-CE than 4-CE was observed. In women with breast carcinoma, the 4-CE were 3.5 times more abundant than the 2-CE and were 4 times higher than in the women without breast cancer. Furthermore, a statistically lower level of methylation was observed for the CE in cancer cases compared to controls. Finally, the level of CE-Q conjugates in women with cancer was 3 times that in controls, suggesting a larger probability for the CE-Q to react with DNA in the breast tissue of women with carcinoma. These data suggest that initiation of human breast cancer is due to imbalances in estrogen homeostasis that result in excessive formation of the electrophilic CE-Q. In particular, the CE-3,4-Q can react with DNA to generate successively depurinating adducts, apurinic sites and oncogenic mutations leading to breast cancer. (Badawi A. F., et al., *Proc. Amer. Assoc. Cancer Res.*, 42, 664 (2001).)

*Health*, 5, 785-792 (1979); Snyder, R. and Kalf, G. F., *CRC Crit. Rev. Toxicol.*, 24, 177-209 (1994); Koop, D. R., et al., *Toxicol. Appl. Pharmacol.*, 98, 278-288 (1989); Guengerich, F. P., et al., *Chem. Res. Toxicol.*, 4, 168-179 (1991); Sabourin, P. J., et al., *Toxicol. Appl. Pharmacol.*, 99, 421-444 (1989); Latriano, L., et al., *Proc. Natl. Acad. Sci. USA*, 83, 8356-8360 (1986); Schlosser, P. M., *Carcinogenesis*, 14, 2477-2486 (1993); Rickert, D. E., et al., *Toxicol. Appl. Pharmacol.*, 49,

TABLE 4

Estrogen metabolites and conjugates in breast tissue from women with and without breast cancer

| Breast Tissue | Compounds,[a] pmol/g tissue | | | | | | |
|---|---|---|---|---|---|---|---|
| | $4\text{-}OHE_1(E_2)$ | $2\text{-}OHE_1(E_2)$ | $\dfrac{4\text{-}OHE_1(E_2)}{2\text{-}OHE_1(E_2)}$ | $4\text{-}OMeE_1(E_2)$ | $2\text{-}OMeE_1(E_2)$ | $4\text{-}+2\text{-}OMeE_1(E_2)$ | CE-Q conjugates |
| Controls[b] | 3.6 ± 2.1 (10)[c] | 6.9 ± 6.1 (25) | 0.52 | 4.9 ± 1.8 (24) | 3.6 ± 2.3 (16) | 8.5 | 2.6 ± 1.3 (29) |
| Breast cancer cases[b] | 14.7 ± 11.5 (53) | 4.2 ± 4.6 (46) | 3.5 | 3.1 ± 2.3 (39) | 1.7 ± 1.0 (29) | 4.8 | 8.2 ± 6.4 (57) |
| p[d] | 0.047 | n.s.[e] | | 0.049 | 0.050 | | 0.003 |

[a]The notation $E_1(E_2)$ indicates that the metabolites, conjugates or adducts of both $E_1$ and $E_2$ were detected.
[b]Controls include 18 women with benign breast tissue and 31 with benign fibrocystic changes for a total of 49 women. Breast cancer cases include 28 women with carcinoma of the breast.
[c]Number in parentheses indicates the percentage of specimens in which the compound was detected.
[d]p was calculated by the student's t-test.
[e]n.s.: not significant.

Unifying Mechanism of Initiation of Cancer and Other Diseases

Figure 8A:
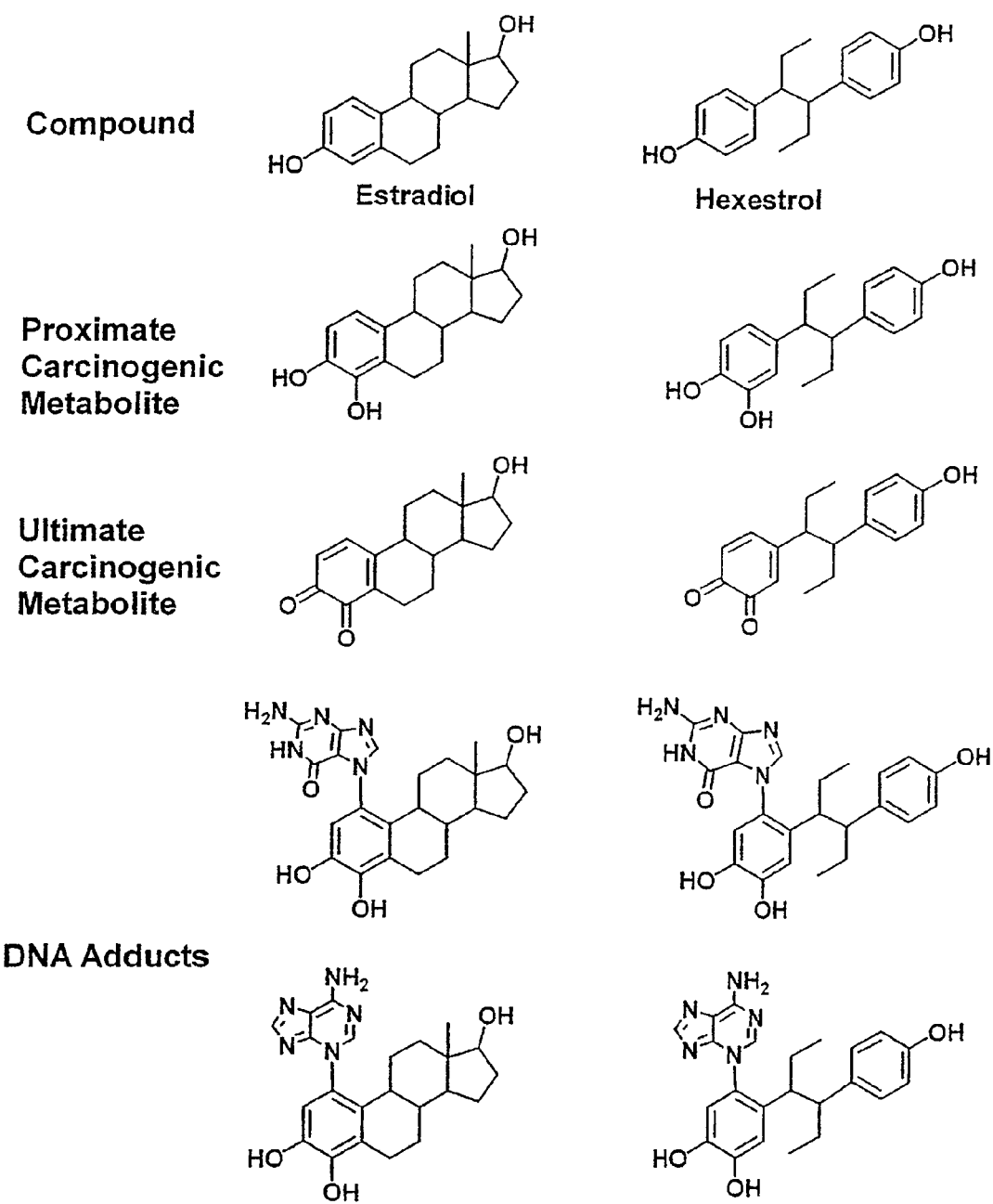
FIGS. 8A-B demonstrate a unifying mechanism of activation and formation of DNA adducts. (A) Natural and synthetic estrogens, and (B) Benzene and dopamine.

Oxidation of catechols to semiquinones and quinones is a postulated pathway to initiate cancer not only with endogenous estrogens but also with synthetic estrogens such as the human carcinogen diethylstilbestrol and its hydrogenated derivative hexestrol. In fact, these two compounds are also carcinogenic in the kidney of Syrian golden hamsters, and the major metabolites are their catechols. These catechols may be metabolically converted to catechol quinones. The catechol quinone of hexestrol has chemical and biochemical properties similar to those of CE-3,4-Q, namely, it specifically forms N7Gua and N3Ade adducts by 1,4-Michael addition after reaction with dG or Ade, respectively, as well as DNA (FIG. 8A). These data suggest that the hexestrol catechol quinone is the electrophile involved in tumor initiation by hexestrol. In turn, these results substantiate the hypothesis that CE-3,4-Q may be the major endogenous tumor initiators. (Herbst A. L., et al., *New Engl. J. Med.*, 284, 878-881 (1971); Li, J. J., et al., *Cancer Res.*, 43, 5200-5204 (1983); Liehr J. G., et al., *Chem.-Biol. Interactions*, 55, 157-176 (1985); Haaf H. and Metzler M., *Pharmacol.*, 34, 3107-3115 (1985); Blaich, G., et al., *J. Steroid Biochem.*, 35, 201-204 (1996); Metzler M. and McLachlan J. A., *Adv. Exp. Med. Biol.*, 136A, 829-837 (1981); Jan S.-T., et al., *Chem. Res. Toxicol*, 11, 412-419 (1998) and unpublished results).

Figure 8B:
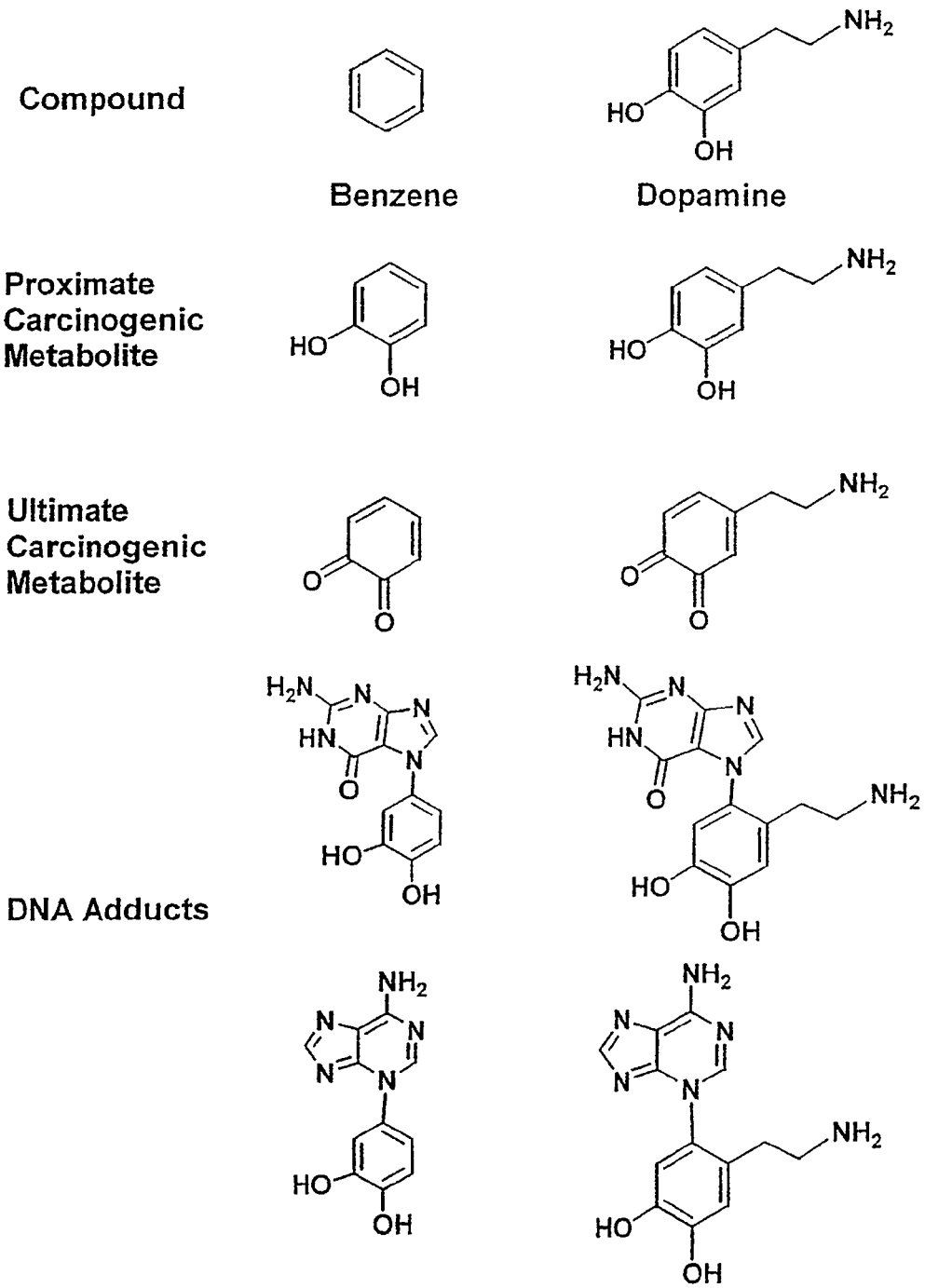

The oxidation of phenols to catechols and then to semiquinones and quinones is not only a mechanism of tumor initiation for natural and synthetic estrogens, but it could also be the mechanism of tumor initiation for the leukemogen benzene (FIG. 8B). Certain metabolites of benzene may be responsible for both its cytotoxic and genotoxic effects. Benzene is metabolized to phenol in the liver by cytochrome P450 2E1. Other metabolites include catechol, hydroquinone (1,4-dihydroxybenzene) and muconaldehyde. Catechol and hydroquinone accumulate in the bone marrow, where they can be oxidized by peroxidases, including myeloperoxidase and prostaglandin H synthase. The resulting quinones can yield DNA adducts. (Andrews, et al., *Biochem. Pharmacol.*, 26, 293-300 (1977); Sammett, D., et al., *J. Toxicol. Environ.* 417-423 (1979); Greenlee, W. F., et al., *Chem.-Biol. Interact.*, 33, 285-299 (1981); Eastmond, D. A., et al., *Mol. Pharmacol.*, 30, 674-679 (1986); Subrahmanyam, V. V., *Arch. Biochem. Biophys.*, 286, 76-84 (1991); Sadler, A., et al., *Toxicol. Appl. Pharmacol*, 93, 62-71 (1988); Schlosser, M. J., et al., *Chem. Res. Toxicol.*, 3, 333-339 (1990); Levay, G., et al., *Carcinogenesis*, 12, 1181-1186 (1991); Levay, G. and Bodell, W. J., *Proc. Natl. Acad. Sci. USA*, 89, 7105-7109 (1992); Levay, G., et al., *Carcinogenesis*, 14, 2329-2334 (1993).)

In fact, catechol, one of the metabolites of benzene, when oxidized to catechol quinone, reacts with dG and Ade to form the catechol-4-N7Gua and catechol-4-N3Ade adducts in high yields, respectively. Oxidation of catechol catalyzed by horseradish peroxidase, tyrosinase or phenobarbital-induced rat liver microsomes in the presence of DNA yielded the catechol-4-N7Gua adduct, while the catechol-4-N3Ade adduct was obtained only with tyrosinase. (Balu N., et al., *Proc. Amer. Assoc. Cancer Res.*, 40, 46 (1999); Cavalieri, E. L., et al., *Carcinogenesis*, in press (2002).)

Catecholamine neurotransmitters such as dopamine may produce semiquinones and quinones via autoxidation, metal ion oxidation and peroxidative enzyme or cytochrome P450 oxidation. This oxidative process is similar to the one described for the benzene metabolite catechol and the 4-CE, and it may initiate Parkinson's disease and other neurodegenerative disorders. The etiology of Parkinson's disease and the basic mechanism of loss of dopamine neurons are unknown. One of the functions of dopamine is the synthesis of neuronmelanin via oxidation of dopamine to its quinone. If oxidation of dopamine to its quinone does not occur in a properly controlled environment, dopamine quinone may react with DNA to cause damage by formation of specific depurinating adducts. In fact, N7Gua and N3Ade adducts (FIG. 8B) are obtained by reaction of the dopamine quinone with dG or Ade, respectively, and the same adducts are formed when dopamine is enzymatically activated in the presence of DNA. The mutations generated by this damage may play a role in the initiation of Parkinson's disease and other neurodegenerative disorders. (Mattammal M. B., et al., *J. Neurochem.*, 64, 1845-1854 (1995); Kalyanaraman B., et al., *Environ.*

*Health Perspect.*, 64, 185-194 (1985); Kalyanaraman B., et al., *J. Biol. Chem.*, 259, 7584-7589 (1984); Balu N., et al., *Proc. Amer. Assoc. Cancer Res.*, 40, 46 (1999); Cavalieri, E. L., *Carcinogenesis*, in press (2002)).

Conclusions

The carcinogenicity of estrogens in animal models led to an investigation of the plausible estrogen metabolites that could react with DNA and lead to mutations initiating cancer. The electrophilic CE-3,4-Q can, indeed, react with DNA to form the specific depurinating adducts bonded at the N-7 of Gua and N-3 of Ade. The apurinic sites formed by depurinating adducts are converted into tumor-initiating mutations by error-prone repair. The specificity of the reaction of the electrophiles with DNA is not limited to the natural estrogens, but also includes the carcinogenic synthetic estrogens such as hexestrol. In this case metabolic formation of its catechol and further oxidation to its catechol quinone lead to formation of analogous specific depurinating adducts at the N-7 of Gua and N-3 of Ade. In addition, the metabolite catechol of the leukomogenic benzene and the catecholamine neurotransmitter dopamine, when oxidized to quinone, binds to DNA to form N7Gua and N3Ade adducts. (Cavalieri E., et al., Estrogens as endogenous genotoxic agents: DNA adducts and mutations. In: JNCI Monograph 27: Estrogens as Endogenous Carcinogens in the Breast and Prostate, 75-93, E. Cavalieri and E. Rogan (eds.), Oxford Press, Washington (2000); Chakravarti D., et al., *Mutation Res.*, 456: 17-32 (2000); Chakravarti D. et al., *Oncogene*, 20: 7945-7953 (2001); Jan S.-T., et al., *Chem. Res. Toxicol*, 11: 412-419 (1998).)

Thus, a unifying mechanism, namely, formation of catechol quinones and reaction with DNA by 1,4-Michael addition to yield depurinating adducts, is at the origin of cancers induced by oxidation of endogenous and synthetic estrogens, leukemia by oxidation of benzene, and neurodegenerative diseases by oxidation of dopamine. This unifying mechanism provides targets for disease prevention and treatment, and methods to assess risk of developing diseases and/or their progression.

Example II

Catechol Ortho-Quinones: The Electrophilic Compounds that Form Depurinating DNA Adducts and Could Initiate Cancer and Other Diseases Introduction An important pathway in the metabolism of catechol estrogens (CE) and catecholamines is the oxidation to their respective semiquinones and quinones. The basis of the biological activity of catechol quinones is related to their ability to act both as oxidants and electrophiles. As oxidants, catechol quinones redox cycle with their semiquinones, producing an elevated level of reactive oxygen species, a condition known as oxidative stress. As electrophiles, catechol quinones can form covalent adducts with cellular macromolecules, including DNA. These are stable adducts that remain in DNA unless removed by repair and depurinating ones that are released from DNA by destabilization of the glycosyl bond. Thus, DNA can be damaged by the reactive quinones themselves and by reactive oxygen species (hydroxyl radicals). The formation of depurinating adducts by CE quinones reacting with DNA may be a major event in the initiation of breast and other human cancers. The depurinating adducts are released from DNA, leaving apurinic sites in the DNA that can generate mutations leading to cancer. (Liehr, J. G. and Roy, D., *Free Radic. Biol. Med.*, 8, 415-423 (1990); Cavalieri, E. L. and Rogan, E. G., The key role of catechol estrogen-3,4-quinones in tumor initiation. In Creveling, C.R. (ed). Role of Catechol Quinone Species in Cellular Toxicity, F.P. Graham Pub. Co., Johnson City, Tenn., 247-260 (2000); Finley, K. T., Quinones: The present state of addition and substitution chemistry. In Patai, S. (ed.) The chemistry of hydroxyl, ether and peroxide groups, John Wiley & Sons Ltd., Suppl. E, 1027-1134 (1993); Cavalieri, E. L., et al., *Proc. Natl. Acad. Sci. USA*, 94, 10937-10942 (1997); Cavalieri, E., et al., Estrogens as endogenous genotoxic agents: DNA adducts and mutations. In Cavalieri, E. and Rogan, E. (eds.) JNCI Monograph: "Estrogens as endogenous carcinogens in the breast and prostate", Oxford University Press, 75-93 (2000); Chakravarti, D., et al., *Proc. Natl. Acad. Sci. USA*, 92, 10422-10426 (1995); Chakravarti, D., *Mutat. Res.*, 456, 17-32 (2000); Chakravarti, D., et al., *Oncogene*, 20, 7945-7953 (2001).)

Figure 9:
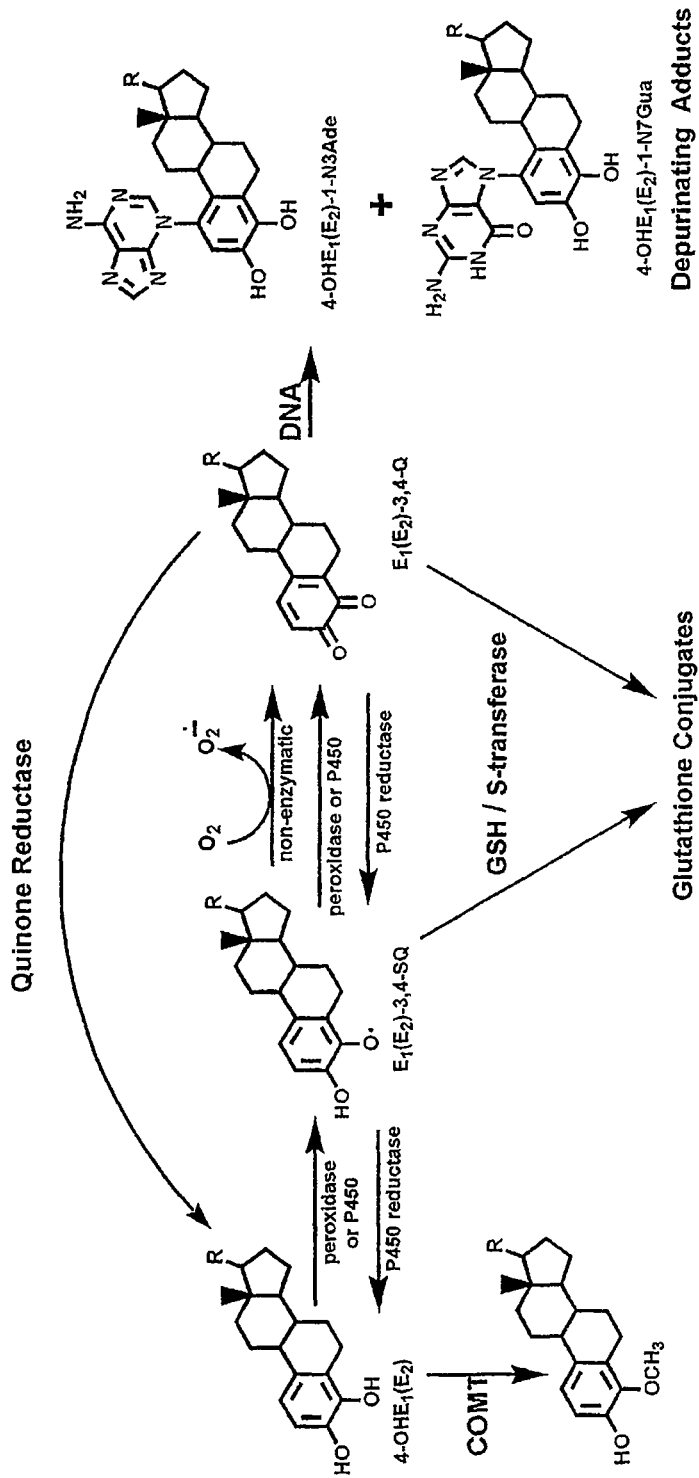
FIG. 9 demonstrates metabolism of 4-$OHE_1(E_2)$ and formation of depurinating DNA adducts.

An important metabolic pathway of the estrogens, estrone ($E_1$) and estradiol ($E_2$), is formation of CE, namely, the hydroxylated estrogens, 4-hydroxyestrone(estradiol) [4-OHE$_1$(E$_2$)], which are carcinogenic in animals, and the isomeric 2-OHE$_1$(E$_2$). Oxidation of 4-OHE$_1$(E$_2$) to their quinones [E$_1$(E$_2$)-3,4-Q] and reaction with DNA form the 4-OHE$_1$(E$_2$)-1-N7guanine (Gua) and 4-OHE$_1$(E$_2$)-1-N3adenine (Ade) adducts by depurination (FIG. 9). (Liehr, J. G., et al., *J. Steroid Biochem.*, 24, 353-356 (1986); Li, J. J. and Li, S. A., *Fed. Proc.*, 46, 1858-1863 (1987); Cavalieri, E. L., et al., *Proc. Natl. Acad. Sci. USA*, 94, 10937-10942 (1997); Cavalieri, E., et al., Estrogens as endogenous genotoxic agents: DNA adducts and mutations. In Cavalieri, E. and Rogan, E. (eds.) JNCI Monograph: "Estrogens as endogenous carcinogens in the breast and prostate", Oxford University Press, pp. 75-93 (2000); Li, K.-M., et al., *Proc. Amer. Assoc. Cancer Res.*, 39, 636 (1998).)

Benzene

Benzene is carcinogenic and leukemogenic in rats and mice, and epidemiological studies have established a relationship between exposure to benzene and acute myelogenous leukemia in humans. Several studies indicate that certain metabolites of benzene are responsible for both its cytotoxic and genotoxic effects. High levels of peroxidase and a lack of quinone reductase in the bone marrow allow formation of toxic semiquinones and quinones without the possibility of their being reduced. Benzene is initially metabolized to phenol in the liver by cytochrome P450 2E1. Other metabolites include catechol (CAT, 1,2-dihydroxybenzene), hydroquinone (1,4-dihydroxybenzene) and muconaldehyde. Several studies have shown that CAT and hydroquinone accumulate in bone marrow, where they can be further activated to exert their myelotoxic effects. (Cronkite, E. P., et al., *Environ. Health Perspect.*, 82, 97-108 (1989); Maltoni, C., et al., *Environ. Health Perspect.*, 82, 109-124 (1989); Huff, J. E., et al., *Environ. Health Perspect.*, 82, 125-163 (1989); (IARC, *IARC Monographs on the Evaluation of the Carcinogenic Risk of Chemicals to Humans* 29, 93-148 (1982); Rinsky, R. A., et al., *N. Engl. J. Med.*, 316, 1044-1050 (1987); Andrews, L. S., et al., *Biochem. Pharmacol.*, 26, 293-300 (1977); Sammett, D., et al., *J. Toxicol. Environ. Health*, 5, 785-792 (1979); Kalf, G. F., *CRC Crit. Rev. Toxicol.*, 18, 141-159 (1987); Snyder, R. and Kalf, G. F., *CRC Crit. Rev. Toxicol.*, 24, 177-209 (1994); Twerdok, L. E. and Trush, M. A., *Res. Commun. Chem. Pathol. Pharmacol.*, 67, 375-386 (1990); Koop, D. R., et al., *Toxicol. Appl. Pharmacol.*, 98, 278-288 (1989); Guengerich, F. P., et al, *Chem. Res. Toxicol.*, 4, 168-179 (1991); Sabourin, P. J., et al., *Toxicol. Appl. Pharmacol.*, 99, 421-444 (1989); Latriano, L., et al., *Proc. Natl. Acad. Sci. USA*, 83, 8356-8360 (1986); Schlosser, P. M., et al., *Carcinogenesis*, 14, 2477-2486 (1993); Rickert, D. E., et al., *Toxicol. Appl. Pharmacol.*, 49, 417-423

(1979); Greenlee, W. F., et al., *Chem.-Biol. Interact.*, 33, 285-299 (1981); Kalf, G. F., *CRC Crit. Rev. Toxicol.*, 18, 141-159 (1987); Eastmond, D. A., *Mol. Pharmacol.*, 30, 674-679 (1986); Subrahmanyam, V. V., et al., *Arch. Biochem. Biophys.*, 286, 76-84 (1991); Sadler, A., et al., *Toxicol. Appl. Pharmacol.*, 93, 62-71 (1988); Schlosser, M. J., et al., *Chem. Res. Toxicol.*, 3, 333-339 (1990); Levay, G., et al., *Carcinogenesis*, 12, 1181-1186 (1991); Levay, G. and Bodell, W. J., *Proc. Natl. Acad. Sci. USA*, 89, 7105-7109 (1992); Levay, G., et al., *Carcinogenesis*, 14, 2329-2334 (1993).)

Dopamine

The neurotransmitter DA is formed in the cell bodies of the dopaminergic neurons of the substantia nigra. Degeneration of the nigrostriatal dopaminergic neurons and decreased production of DA results in Parkinson's disease. The etiology of Parkinson's disease and its underlying mechanism of loss of DA neurons are unknown. There is evidence, however, that DA is involved in the etiology of this disease, based on the observation by Graham, et al. that DA is oxidized to the corresponding quinone. Injection of DA into neostriatum generates toxicity to dopaminergic neurons, and the toxicity correlates with protein binding. Glutathione and ascorbic acid diminish the toxicity of protein binding. Covalent binding of DA to DNA occurs upon incubating DA with HL-60 cells or human glioblastoma cell lines, by copper-mediated oxidation of DA or by oxidation of DA with prostaglandin H synthase. (Graham, D. G., et al., *Mol. Pharmacol.*, 14, 644-653 (1978); Hastings, T. G., et al., *Proc. Natl. Acad. Sci. USA*, 93, 1956-1961 (1996); Filloux, F. and Townsend, J. J., *Exper. Neurol.*, 119, 79-88 (1993); Hastings, T. G. and Zigmond, M. J., *J. Neurochem.*, 63, 1126-1132 (1994); Levay, G. and Bodell, W. J., *Carcinogenesis*, 14, 1241-1245 (1993); Levay, G., et al., *Exper. Neurol.*, 146, 570-574 (1997); Hastings, T. G., *J. Neurochem.*, 64, 919-924 (1995); Mattammal, M. B., *J. Neurochem.*, 64, 1845-1854 (1995).)

Oxidation of DA to its quinone and subsequent reaction with DNA may cause DNA damage via formation of specific depurinating adducts, and the mutations generated by that damage may play a major role in initiating the series of events leading to neurodegenerative disorders such as Parkinson's disease. In general, catecholamine neurotransmitters such as DA can produce semiquinones and quinones via autoxidation, metal ion oxidation, and peroxidative enzyme or cytochrome P450 oxidation. This oxidative process is similar to the one described above for the benzene metabolite CAT and for the 4-OHE$_1$(E$_2$) formed by the metabolism of E$_1$ and E$_2$. (Kalyanaraman, B., et al., *Environ. Health Perspect.*, 64, 185-194 (1985); Kalyanaraman, B., et al., *J. Biol. Chem.* 259, 7584-7589 (1984); Cavalieri, E. L., et al., *Proc. Natl. Acad. Sci. USA*, 94, 10937-10942 (1997); Cavalieri, E., et al., Estrogens as endogenous genotoxic agents: DNA adducts and mutations. In Cavalieri, E. and Rogan, E. (eds.) JNCI Monograph: "Estrogens as endogenous carcinogens in the breast and prostate", Oxford University Press, 75-93 (2000).)

Abbreviations

Ade, adenine; o-BQ, ortho-benzoquinone; CAT, catechol or 1,2-dihydroxybenzene; CE, catechol estrogen(s); CE-Q, catechol estrogen quinone(s); COMT, catechol-O-methyltransferase; DA, dopamine; dG, deoxyguanosine; DMF, dimethylformamide; E$_1$, estrone; E$_2$, estradiol; E$_1$(E$_2$)-3,4-Q, estrone(estradiol)-3,4-quinones or catechol estrogen-3,4-quinones; FAB, fast atom bombardment; Gua, guanine; MS/MS, tandem mass spectrometry; NADA, N-acetyldopamine; OHE$_1$(E$_2$), hydroxyestrone(estradiol); TFA, trifluoroacetic acid.

Definitions

The term catechol refers to an aromatic ring with vicinal hydroxyl substituents. Herein catechol is spelled out when it is used in a general sense. When it refers specifically to the compound 1,2-dihydroxybenzene, normally called catechol, it is abbreviated CAT.

Materials and Methods

Chemicals, Reagents and Enzymes:

CAT was obtained from ICN Pharmaceuticals Inc., Cleveland, Ohio; Ag$_2$O, NaIO$_4$, Ade, thymidine, deuterated acetic acid and trifluoroacetic acid (TFA) were purchased from Aldrich Chemical Co., Milwaukee, Wis. 2'-Deoxyguanosine (dG), 2'-deoxyadenosine and 2'-deoxycytidine were purchased from TCI Chemicals. DA, and N-acetyldopamine (NADA), horseradish peroxidase (type VI) and mushroom tyrosinase were purchased from Sigma Chemicals, St. Louis, Mo. Liver microsomes from phenobarbital-induced female Wistar MRC rats (Eppley Colony) were prepared by the previously published method (Wong, A. K. L., et al., *Biochem. Pharmacol.*, 35, 1583-1588 (1986).)

Instrumentation

UV:

The UV spectra were obtained during HPLC by using the photodiode array detector (Waters 996, Milford, Mass.) for all compounds synthesized. HPLC separations were monitored at 280 nm.

NMR:

Proton and homonuclear two-dimensional chemical shift correlation spectroscopy NMR spectra were recorded in DMSO-d$_6$ with one drop of D$_2$O and one drop of CD$_3$COOD on a Varian Unity 500 instrument at 499.835 MHz at 25° C. Chemical shifts are reported relative to DMSO (2.5 ppm).

Mass Spectrometry:

Exact mass measurements of fast atom bombardment (FAB)-produced ions were carried out on a Kratos MS-50 double focusing mass spectrometer in a peak-match mode. Confirmation of the presence of each adduct was by capillary HPLC coupled via electrospray ionization with a Finnigan LCQ ion trap mass spectrometer operating in the tandem mass spectrometry (MS/MS) mode. The HPLC (Microtech Scientific) made use of a binary gradient of solvent A [0.5% CH$_3$COOH (v/v) in H$_2$O] and solvent B [0.5% CH$_3$COOH (v/v) in CH$_3$OH] at a flow rate of 40 µL/min with a split of 10:1. The column was 0.3×100 Zorbax C18 (Microtech Scientific) with a flow rate on the column of 4 µL/min. The gradient was 95% A/5% B initially for 4 min, then linearly adjusted to 60/40 over 14 min, and held at 60/40 for 20 min.

HPLC Methods for Synthetic Standards:

HPLC was conducted on a Waters (Milford, Mass.) 600 E system equipped with a Waters 996 photodiode array detector interfaced with an NEC-Powermate computer. Analyses and preparative separations were carried out on reverse-phase C-18, YMC (Morris Plains, N.J.) columns (5 µm, 120A, ODS-AQ (6×250 mm) and ODS-AQ, 5 µm, 120 A, (20×250 mm), respectively) using specific mobile phases for the different compounds.

Synthesis of Standard Adducts

Catechol Adducts.

Because the ortho-benzoquinone (o-BQ, nascent quinone) is rather unstable, various methods of synthesis were tested to obtain its maximum yield. Oxidation of CAT using Ag$_2$O in dry dimethylformamide (DMF) was the best method. A solution of CAT (100 mg, 0.91 mmol) in dry DMF (7.5 mL) was stirred with Ag$_2$O (842 mg, 3.60 mmol) for 30 min at 0° C. The extent of formation of o-BQ was followed by HPLC, using a linear analytical gradient from 100% H$_2$O (0.01% TFA, pH 2.6) to 30% CH$_3$CN in 60 min at a flow rate of 1 mL/min (monitored by UV absorbance at 300 nm on a Waters 996 photodiode array detector). The yield of o-BQ was >95%.

Figure 10:
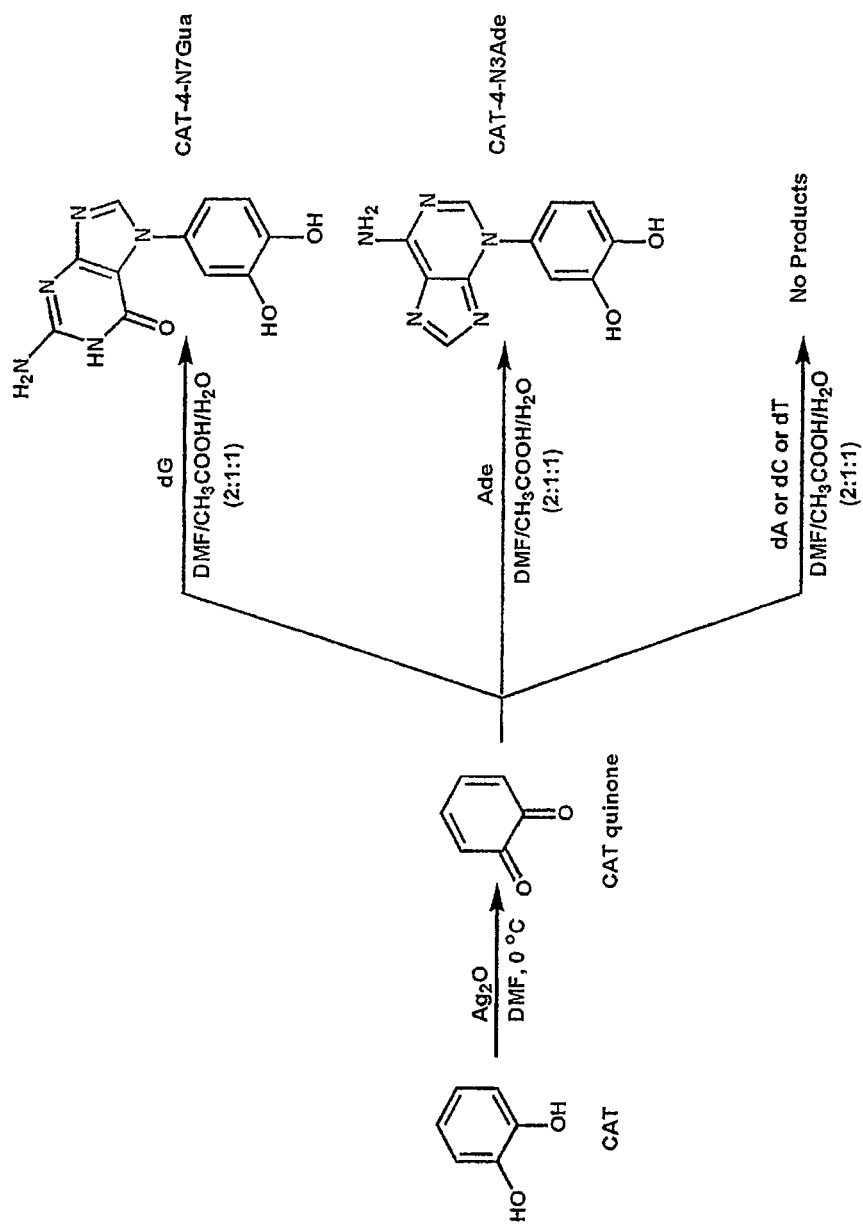
FIG. 10 depicts the synthesis of CAT-4-N7Gua and CAT-4-N3Ade by reaction of CAT quinone with dG or Ade.

The dark red solution was immediately filtered into a solution of dG (1.20 g, 4.54 mmol) or Ade (613 mg, 4.54 mmol) in DMF/CH$_3$COOH/H$_2$O, 7.5 mL each (FIG. 10). The reaction mixture was stirred for 8 h at room temperature, filtered and washed with 10 mL of DMF/CH$_3$COOH/H$_2$O (2:1:1). The reddish-brown filtrate was directly subjected to HPLC purification, using a linear preparative gradient of 20% CH$_3$CN in H$_2$O (0.01% TFA) to 80% CH$_3$CN in H$_2$O (0.01% TFA) over 60 min at a flow rate of 9 mL/min with dG or 15% CH$_3$CN in H$_2$O (0.01% TFA) to 60% CH$_3$CN in H$_2$O (0.01% TFA) over 60 min at a flow rate of 9 mL/min with Ade. The products, isolated under an argon atmosphere and stored at −20° C. in 2 mL of DMF/CH$_3$COOH/H$_2$O (2:1:1), were CAT-4-N7Gua and CAT-4-N3Ade, the result of a 1,4-Michael addition between dG or Ade and o-BQ.

For CAT-4-N7Gua, the yield was 59%; UV: $\lambda_{max}$, 285 nm. $^1$H NMR, δ (ppm): 6.79 (s, 2H, 5-H, 6-H), 7.08 (s, 1H, 3-H), 8.01 (s, 1H, 8-H [Gua]). FAB MS, [M+H]$^+$, C$_{11}$H$_9$N$_5$O$_3$: calcd m/z 260.0785; obsd m/z 260.0783.

For CAT-4-N3Ade, the yield was 65%; UV: $\lambda_{max}$, 279 nm. $^1$H NMR, δ (ppm): 6.95 (bd, 2H, 5-H, 6-H), 7.08 (s, 1H, 3-H), 8.52 (s, 1H, 2-H [Ade]), 8.76 (s, 1H, 8-H [Ade]). FAB MS, [M+H]$^+$, C$_{11}$H$_9$N$_5$O$_2$: calcd m/z 244.0836; obsd m/z 244.0834.

N-Acetyldopamine Adducts.

Figure 11:
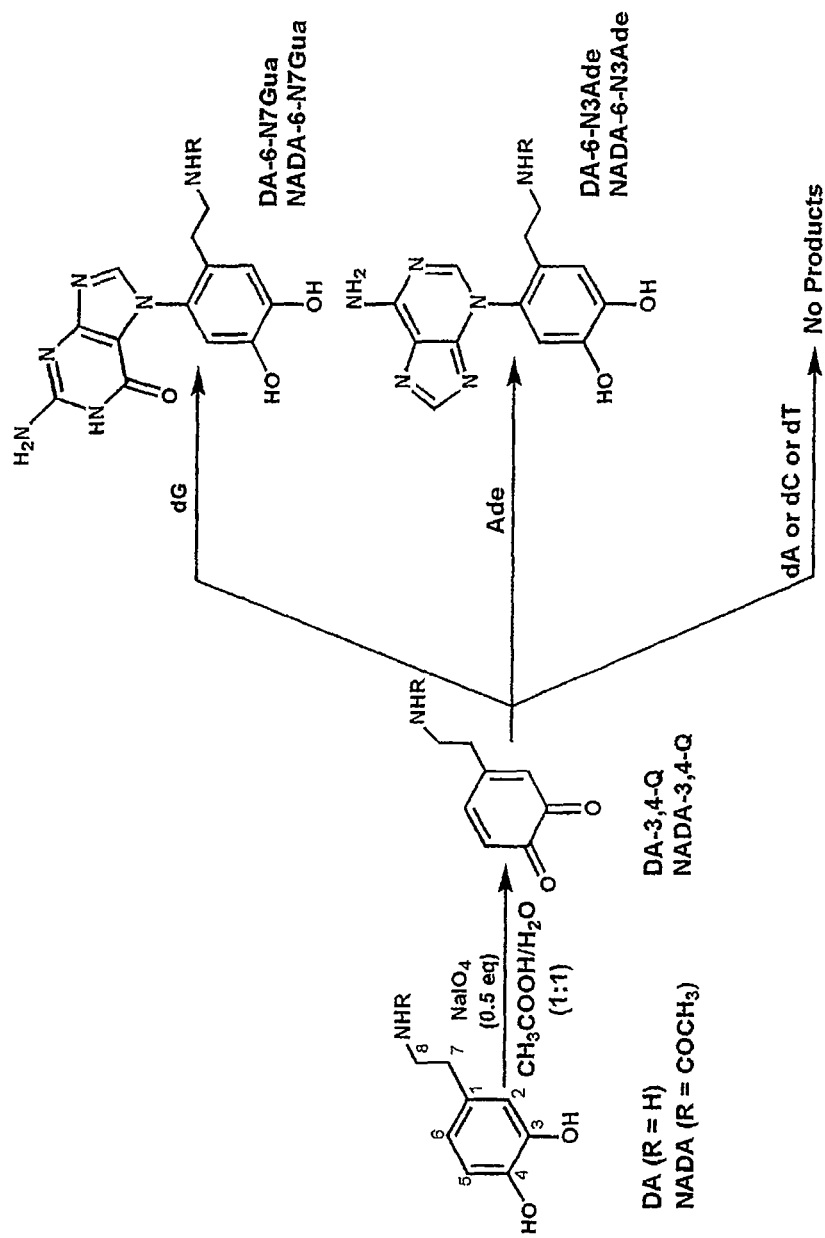
FIG. 11 demonstrates the synthesis of DA (NADA)-6-N7Gua and DA (NADA)-6-N3Ade by reaction of DA (NADA) quinone with dG or Ade.

A solution of NADA (9 mg, 0.047 mmol) in 1.5 mL of CH$_3$COOH/H$_2$O (1:1) was stirred with NaIO$_4$ (5 mg, 0.023 mmol) for 5 min at room temperature. To the resulting red solution of the NADA quinone was added 5 equivalents of dG (59 mg, 0.23 mmol) in 1.5 mL of CH$_3$COOH/H$_2$O (1:1) (FIG. 11). The reaction mixture was stirred for 3 h at room temperature and then separated by HPLC, using a 45-min linear preparative gradient from 10% CH$_3$CN in H$_2$O (0.01% TFA) to 30% CH$_3$CN in H$_2$O (0.01% TFA) at a flow rate of 10 mL/min. The yield of NADA-6-N7Gua was 58%.

The NADA-6-N7Gua adduct was also synthesized following oxidation of NADA by Ag$_2$O. A solution of NADA (5 mg, 0.023 mmol) in 1 mL of dry DMF was stirred with Ag$_2$O (43 mg, 0.19 mmol) for 30 min. The suspension was immediately filtered into a solution of dG (29 mg, 0.12 mmol) in DMF/CH$_3$COOH/H$_2$O, 1 mL each. The reaction mixture was stirred for 10 h at room temperature, and the product purified by HPLC, yielding 60% NADA-6-N7Gua, UV: $\lambda_{max}$, 245, 284 nm. $^1$H NMR, δ (ppm): 1.90 (s, 3H, CH$_3$), 2.25 (t, 2H, J=6.7 Hz, 7-CH$_2$), 3.00 (bt, 2H, 8-CH$_2$), 6.62 (s, 1H, 5-H), 6.66 (s, 1H, 2-H), 7.85 (s, 1H, 8-H [Gua]). FAB MS, [M+H]$^+$, C$_{15}$H$_{17}$N$_6$O$_4$: calcd m/z 345.1311; obsd m/z 345.1311.

To synthesize the Ade adduct, a solution of NADA (20 mg, 0.094 mmol) in 2 mL of CH$_3$COOH/H$_2$O (1:1) was oxidized with NaIO$_4$ (10 mg, 0.047 mmol) and reacted with Ade (63 mg, 0.47 mmol), as described above for the reaction with dG. The product, NADA-6-N3Ade, was purified by HPLC, using a preparative linear gradient from 5% CH$_3$CN in H$_2$O (0.01% TFA) over 60 min to 40% CH$_3$CN in H$_2$O (0.01% TFA) at a flow rate of 9 mL/min. The yield was 51%; UV: $\lambda_{max}$, 275 nm. $^1$H NMR, δ (ppm): 1.90 (s, 3H, CH$_3$), 2.15-2.30 (m, 2H, 7-CH$_2$), 2.83-3.10 (m, 2H, 8-CH$_2$), 6.81 (s, 1H, 5-H), 6.85 (s, 1H, 2-H), 8.45 (s, 1H, 2-H [Ade]), 8.65 (s, 1H, 8-H [Ade]). FAB MS, [M+H]$^+$, C$_{15}$H$_{17}$N$_6$O$_3$: calcd m/z 329.1361; obsd m/z 329.1362.

Dopamine Adducts.

DA.HCl (50 mg, 0.264 mmol) and dG (622 mg, 2.6 mmol) were dissolved in 13 mL of CH$_3$COOH/H$_2$O (1:1). To this mixture a solution of NaIO$_4$ (28 mg, 0.13 mmol) in 2 mL of CH$_3$COOH/H$_2$O (1:1) was added dropwise over 10 min (FIG. 11). After 3 h at room temperature, the reaction was terminated, and the product, DA-6-N7Gua, was purified by preparative HPLC, using a linear gradient from 10% CH$_3$CN in H$_2$O (0.01% TFA) to 30% CH$_3$CN in H$_2$O (0.01% TFA) over 60 min, then to 80% CH$_3$CN in 15 min at a flow rate of 8 mL/min. The colorless semi-solid product was obtained in 46% yield. UV: $\lambda_{max}$, 245 (sh), 283 nm. $^1$H NMR, δ (ppm): 2.45 (m, 2H, 7-CH$_2$), 2.75 (m, 2H, 8-CH$_2$), 6.70 (s, 1H, 5-H), 6.70 (s, 1H, 2-H), 8.15 (s, 1H, 8-H [Gua]). FAB MS, [M+H]$^+$, C$_{13}$H$_{14}$N$_6$O$_3$: calcd m/z 303.1207; obsd m/z 303.1205.

A solution of DA.HCl (50 mg, 0.26 mmol) and Ade (356 mg, 2.64 mmol) in 13 mL of CH$_3$COOH/H$_2$O (1:1) was treated with a solution of NaIO$_4$ (28 mg, 0.13 mmol) in 2 mL of CH$_3$COOH/H$_2$O (1:1) in a manner similar to that used to synthesize DA-6-N7Gua. After 3 h at room temperature, the reaction was terminated. The mixture was subjected to preparative HPLC, using H$_2$O (0.01% TFA) at a flow rate of 5 mL/min for 20 min, followed by a linear gradient to 80% CH$_3$CN in H$_2$O (0.01% TFA) over 40 min at a flow rate of 10 mL/min. DA-6-N3Ade was obtained in 40% yield. UV: $\lambda_{max}$, 279 nm. $^1$H NMR, δ (ppm): 2.40 (m, 2H, 7-CH$_2$), 2.82 (m, 2H, 8-CH$_2$), 6.80 (s, 1H, 5-H), 6.86 (s, 1H, 2-H), 8.05 (s, 1H, 2-H [Ade]), 8.40 (s, 1H, 8-H [Ade]). FAB MS, [M+H]$^+$, C$_{13}$H$_{14}$N$_6$O$_2$: calcd m/z 287.1258; obsd m/z 287.1256.

Enzymatically-Catalyzed Covalent Binding of Catechol and Dopamine to DNA

CAT and DA were bound to DNA in 10-mL reaction mixtures containing 3 mM calf thymus DNA in 0.067 M sodium-potassium phosphate (pH 7.0), 0.8 μM CAT or DA in 50 μL DMSO and 1 mg horseradish peroxidase plus 0.5 mM H$_2$O$_2$ or 1 mg mushroom tyrosinase. CAT and DA (0.8 μM) were also activated by 10 mg of phenobarbital-induced rat liver microsomes in 150 mM Tris-HCl (pH 7.5), 150 mM KCl, 5 mM MgCl$_2$, 1 mM cumene hydroperoxide and 3 mM DNA. The reactions were incubated for 2 h at 37° C. A 1-mL aliquot was used for analysis of stable DNA adducts by the $^{32}$P-postlabeling method with 8 μg of DNA. The DNA was precipitated from the remaining reaction mixture with two volumes of ethanol, and the supernatant was used for structure determination of depurinating adducts. After evaporation under vacuum, the residue was dissolved in 1 mL of DMSO/CH$_3$OH. The CAT adducts were first separated by HPLC on a preparative column with a curvilinear gradient (CV 6) from 100% H$_2$O (0.01% TFA) to 15% CH$_3$OH in H$_2$O (0.01% TFA) in 60 min at a flow rate of 3 mL/min. Fractions at the retention times of CAT-4-N3Ade (34.5 min) and CAT-4-N7Gua (40 min) were collected and analyzed by HPLC, which was eluted with aqueous 50 mM (NH$_4$)$_3$PO$_4$, 5 mM sodium dodecyl sulfate, 1% CH$_3$COOH at a flow rate of 0.5 mL/min. The DA adducts were first separated by HPLC on a preparative column eluted with a curvilinear gradient (CV 6) from 100% aqueous 50 mM (NH$_4$)$_3$PO$_4$, 5 mM sodium dodecyl sulfate, 4% CH$_3$COOH to 100% CH$_3$CN at a flow rate of 0.5 mL/min. Fractions were collected at 34 min for DA-6-N3Ade and 37 min for DA-6-N7Gua and analyzed by HPLC as described above for the CAT adducts. The remainder of the collected fractions was used to confirm the structures of the adducts by MS. (Wong, A. K. L., et al., *Biochem. Pharmacol.*, 35, 1583-1588 (1986); Bodell, W. J., et al., *Chem. Res. Toxicol.*, 2, 312-315 (1989).)

Results

To demonstrate that the quinones of CAT and DA can react with the nucleobases of DNA, standard adducts were synthesized by reaction of o-BQ or DA quinone with dG or Ade. The syntheses provided useful insights into the ability of these electrophilic species to react with nucleophilic groups of deoxyribonucleosides. Furthermore, the adducts served as standards to identify the depurinating adducts formed when CAT and DA were oxidized in vitro by various enzymes in the presence of DNA (see below).

Structure Elucidation of Adducts

Catechol Adducts.

The reaction of o-BQ with the deoxyribonucleoside bases to afford the desired adducts is an acid-assisted 1,4-Michael addition reaction analogous to that of CE quinones with nucleobases. With o-BQ, however, the reaction in $CH_3COOH/H_2O$ (1:1) did not yield any products, due to the instability of o-BQ. To render this reaction feasible a compromise was reached by conducting it in $DMF/CH_3COOH/H_2O$ (2:1:1). (Stack, D., et al., Chem. Res. Toxicol., 9, 851-859 (1996); Jan, S.-T., et al., Chem. Res. Toxicol., 11, 412-419 (1998).)

Reaction of o-BQ with dG afforded CAT-4-N7Gua (FIG. 10). The structure was readily determined by both NMR and MS analysis. By MS, the $[M+H]^+$ ion had an m/z 260, indicating that deoxyribose had been lost. This implies that Gua is bonded to CAT at the N-7. The NMR resonance of the 5-H and 6-H of the CAT moiety as a singlet at 6.79 ppm and the 3-H as a singlet at 7.08 ppm indicates that the bond to Gua in the CAT aromatic ring occurs at C-4.

For CAT-4-N3Ade, the structure was consistent with the NMR spectrum, showing the aromatic protons 5-H and 6-H as a doublet at 6.95 ppm, and the singlet at 7.08 ppm that was assigned as 3-H. Furthermore, the 2-H and 8-H of the Ade moiety were observed at 8.52 and 8.76 ppm, respectively. The mass of the FAB-produced ion at m/z 244 corroborated the structure of this adduct.

Under the same conditions, o-BQ adducts of deoxyadenosine, deoxycytidine and thymidine were not obtained. Furthermore, reaction of the stable 1,4-benzoquinone (p-BQ) with dG, Ade, deoxyadenosine, deoxycytidine or thymidine did not afford any detectable adducts.

Dopamine Adducts.

The oxidation of DA and subsequent reaction with dG or Ade were more difficult to accomplish because the amino group of the DA quinone reacts intramolecularly by a 1,4-Michael addition to produce a dihydroindole, a precursor to neuromelanin biosynthesis. This reaction competes with the intermolecular acid-assisted 1,4-Michael addition of the nucleophilic groups of dG and Ade to the DA quinone. To avoid the competitive cyclization reaction, NADA, in which the nucleophilic amino group of DA is acetylated, was oxidized to its quinone and reacted with deoxyribonucleosides or nucleobases.

N-Acetyldopamine.

The structure of the NADA-6-N7Gua adduct (FIG. 11) was consistent with MS results, which showed an m/z 345 ion, indicating the loss of the deoxyribose moiety. It was also consistent with the NMR results: the two aromatic protons of the NADA moiety, 5-H and 2-H, resonate at 6.62 and 6.70 ppm, respectively, assuming that the reaction was a 1,4-Michael addition. If the reaction occurred by 1,6-addition, however, an adduct at C-2 and/or C-5 of NADA should have been obtained. Reaction at C-2 can be disregarded on the basis that the aromatic protons did not resonate as doublets. The adduct with the Gua-NADA bond at C-5, formed by 1,6-addition, was eliminated from consideration by a nuclear Overhauser enhancement experiment in which the resonance of the 7-$CH_2$ protons at 2.25 ppm was irradiated. This structure would entail that both the resonance signals corresponding to 2-H and 6-H be enhanced. In fact, only the signals corresponding to the 2-H of NADA at 6.70 ppm and the 8-H of the Gua moiety at 7.85 ppm were enhanced. This result unequivocally assigns the structure of the adduct as NADA-6-N7Gua, proving that the reaction is a 1,4-Michael addition. Following the same approach, the structure of NADA-6-N3Ade was assigned.

Dopamine.

Reactions of DA.HCl were set at pH 1.2 in $CH_3COOH/H_2O$ (1:1) to minimize intramolecular 1,4-Michael addition of DA and favor intermolecular 1,4-Michael addition of dG or Ade to the 6 position of DA quinone. Although cyclization was avoided under these conditions, owing to the extensive protonation of the DA amino group, minor side reactions such as dimerization and subsequent oligomerization of the resulting DA quinone could not be eliminated. To minimize these competing reactions and obtain the best yields, the DA o-quinone was generated in situ by adding a solution of $NaIO_4$ to a mixture of DA.HCl and dG or Ade.

The structures of the adducts obtained by reaction of DA quinone with dG or Ade, DA-6-N7Gua and DA-6-N3Ade (FIG. 11), were elucidated following the same criteria adopted for the NADA adducts. Under the above conditions, the DA quinone did not react with deoxyadenosine, deoxycytidine or thymidine to form adducts to any measurable extent.

In conclusion, the reaction of CAT quinone and DA quinone with dG or Ade involves the specific nucleophilic sites of the N-7 of Gua and N-3 of Ade in the 1,4-Michael addition. The reactions of $E_1(E_2)$-3,4-Q with dG or Ade by 1,4-Michael addition exhibit the same specificity, forming N7Gua and N3Ade depurinating adducts (Li, K.-M., et al., Proc. Amer. Assoc. Cancer Res., 39, 636 (1998); Stack, D., Chem. Res. Toxicol., 9, 851-859 (1996).)

Enzymatically-Catalyzed Covalent Binding of Catechol and Dopamine to DNA

Conversion of CAT and DA to their quinones can generally occur by autoxidation, metal-ion oxidation or cytochrome P450 or peroxidase-catalyzed oxidation. In vivo the copper-containing enzyme tyrosinase oxidizes DA to its quinone. To demonstrate binding to DNA in vitro, CAT and DA were oxidized in reactions catalyzed by horseradish peroxidase, tyrosinase or phenobarbital-induced rat liver microsomes in the presence of DNA (Table 5).

TABLE 5

Catechol- and Dopamine-DNA Adducts Formed In Vitro.

| | μmol adduct/mol DNA-P[a] | | |
|---|---|---|---|
| Adduct | Horseradish Peroxidase | Phenobarbital-induced rat liver microsomes | Tyrosinase |
| Catechol | | | |
| CAT-4-N7Gua | 10 | 32 | 110 |
| CAT-4-N3Ade | nd[b] | nd | 2 |
| Stable adducts | 0.64 | 0.02 | 0.21 |
| Dopamine | | | |
| DA-6-N7Gua | 1 | 23 | 6 |
| DA-6-N3Ade | 5 | 9 | 3 |
| Stable adducts | 0.30 | 0.24 | 0.35 |

[a]Values are the average of two determinations that varied by 10-20%.
[b]nd: not detected All three enzymes catalyzed formation of detectable amounts of the depurinating adducts of DA, DA-6-N3Ade and DA-6-N7Gua, as well as the CAT-4-N7Gua depurinating adduct of CAT. In contrast, the CAT-4-N3Ade adduct was detected only after activation by tyrosinase. (Kalyanaraman, B., et al., Environ. Health Perspect., 64, 185-194 (1985); Kalyanaraman, B., et al., J. Biol. Chem., 259, 7584-7589 (1984).)

Formation of the stable adducts of DA was low, less than 5% of the total adducts formed with horseradish peroxidase, 4% of the adducts formed with tyrosinase, and 1% of the adducts formed with microsomes. Similarly, with CAT, stable adducts comprised less than 6% of the total adducts formed with horseradish peroxidase, 0.2% of those formed with tyrosinase, and 0.1% of the adducts formed with microsomes. With DA, the microsomes catalyzed formation of six to seven stable adducts that were separated by the $^{32}$P-postlabeling method, whereas tyrosinase and horseradish peroxidase catalyzed formation of the same stable adduct, which appeared to be one of those formed by the microsomes. With CAT, both the microsomes and horseradish peroxidase formed two adducts separated by $^{32}$P-postlabeling. One of these adducts was detected with activation by both enzymes. This same adduct was the only stable adduct detected when tyrosinase was used to catalyze the binding of CAT to DNA.

Confirmation of the presence of each depurinating adduct reported in Table 5 was by capillary HPLC/tandem mass spectrometry. The unknowns have identical HPLC retention times as the standards and give product-ion spectra of the [M+H]$^+$ ions containing the same two or three intense signals as those of the standards. The product-ion spectrum of the two modified guanine [M+H]$^+$ ions showed that losses of 17 (NH$_3$) and 42 (NC—NH$_2$) occurred for both. The CAT-modified Gua showed an additional loss of 24 (possible via formation of an ion-molecule product in the trap), whereas the DA-modified Gua underwent a loss of 35 (NH$_3$ and H$_2$O). The modified bases isolated from the in vitro experiments showed these same ions. The [M+H]$^+$ ions of the adenines modified with CAT or DA fragmented by losses of 17 and 46, and the unknowns also showed signals for these processes. The product-ion spectra of all the in vitro adducts showed other comparable or weaker signals owing to coeluting interferences from the reaction mixture.

In summary, enzymatic oxidation of CAT or DA in the presence of DNA resulted in the formation of 94-99.9% depurinating CAT adducts or 95-99% depurinating DA adducts.

Discussion

The catechol o-quinones derived from benzene and DA undergo 1,4-Michael addition with the N-7 and N-3 nucleophilic sites of Gua and Ade in DNA, respectively, to form predominantly depurinating adducts analogous to those formed by the E$_1$(E$_2$)-3,4-Q (FIG. 9). These depurinating adducts are by far the major products (94-99.9%) when the two o-quinones are enzymatically obtained from the corresponding catechols, CAT and DA, in the presence of DNA (Table 5). (Cavalieri, E. L., et al., *Proc. Natl. Acad. Sci. USA*, 94, 10937-10942 (1997); Li, K.-M., et al., *Proc. Amer. Assoc. Cancer Res.*, 39, 636 (1998).)

The role of estrogens in causing DNA damage is better understood than that of CAT and DA. The estrogens E$_1$ and E$_2$, which are biochemically interconvertible, are metabolized via two major pathways: formation of CE and, to a lesser extent, 16α-hydroxylation. In general, estrogens and CE are inactivated by conjugating reactions, such as glucuronidation and sulfation, especially in the liver. The most common pathway of CE conjugation in extrahepatic tissues is O-methylation catalyzed by the ubiquitous catechol-O-methyltransferase (COMT, FIG. 9). Relatively high levels of cytochrome P450 1B1 and other 4-hydroxylases could cause the 4-OHE$_1$ (E$_2$), which are usually minor metabolites, to be the major ones, rendering conjugation of 4-OHE$_1$(E$_2$) via methylation in extrahepatic tissues insufficient. In this case, competitive catalytic oxidation of CE to CE quinones could occur (FIG. 9). Redox cycling generated by reduction of CE-Q to CE semiquinones, catalyzed by cytochrome P450 reductase, and subsequent oxidation back to CE-Q by molecular oxygen causes formation of superoxide anion radicals and, subsequently, hydroxyl radicals (not shown in FIG. 9). This process, which also occurs with the quinones of CAT and DA, may constitute a significant source of reactive oxygen species. Hydroxyl radicals can also react with DNA and contribute to total DNA damage. (Cavalieri, E., et al., Estrogens as endogenous genotoxic agents: DNA adducts and mutations. In Cavalieri, E. and Rogan, E. (eds.) JNCI Monograph: "Estrogens as endogenous carcinogens in the breast and prostate", Oxford University Press, 75-93 (2000); Cavalieri, E. L., et al., *Proc. Natl. Acad. Sci. USA*, 94, 10937-10942 (1997); Service, R., *Science*, 279, 1631-1633 (1998); Liehr, J. G. and Roy, D., *Free Radic. Biol. Med.*, 8, 415-423 (1990).

CE-Q can be inactivated by conjugation with glutathione (FIG. 9). A second inactivating pathway for CE-Q is their reduction to CE by quinone reductase and/or cytochrome P450 reductase (FIG. 9). If the two inactivating processes are insufficient, CE-Q may react with DNA to form predominantly stable adducts for the 2-OHE$_1$(E$_2$) (not shown in FIG. 9) and predominantly depurinating adducts for the 4-OHE$_1$ (E$_2$) (FIG. 9). The depurinating adducts generate apurinic sites that may lead to oncogenic mutations, thereby initiating a variety of human cancers, including breast and prostate. In support of this hypothesis, a burst of apurinic sites leads to mutations in the H-ras gene of mouse skin treated with E$_2$-3, 4-Q. (DT Diaphorase—A quinone reductase with special functions in cell metabolism and detoxification. Ernester, L., Estabrook, R. W., et al. (eds.) *Chemica Scripta*, 27A (1987); Roy, D. and Liehr, J. G., *J. Biol. Chem.*, 263, 3646-3651 (1988); Cavalieri, E. L., et al., *Proc. Natl. Acad. Sci. USA*, 94, 10937-10942 (1997); Stack, D., et al., *Chem. Res. Toxicol.*, 9, 851-859 (1996); Dwivedy, I., et al., *Chem. Res. Toxicol.*, 5, 828-833 (1992); Li, K.-M., et al., *Proc. Amer. Assoc. Cancer Res.*, 39, 636 (1998); Chakravarti, D., et al., *Proc. Natl. Acad. Sci. USA*, 92, 10422-10426 (1995); Chakravarti, D., et al., *Mutat. Res.*, 456, 17-32 (2000); Chakravarti, D., *Oncogene*, 20, 7945-7953 (2001).)

The initiating mechanism of carcinogenesis for the synthetic estrogen hexestrol may have a similar explanation. This compound, which is carcinogenic in the kidney of Syrian golden hamsters, also has catechol as a major metabolite, which can be metabolically converted to catechol quinone. The catechol quinone of hexestrol has chemical properties similar to those of E$_1$(E$_2$)-3,4-Q, namely, it specifically forms an N7Gua adduct by 1,4-Michael addition after reaction with dG or DNA. (Li, J. J., *Cancer Res.*, 43, 5200-5204 (1983); Liehr, J. G., et al., *Chem.-Biol. Interactions*, 55, 157-176 (1985); Metzler, M. and McLachlan, J. A., *Adv. Exp. Med. Biol.*, 136A, 829-837 (1981); Jan, S.-T., *Chem. Res. Toxicol.*, 11, 412-419 (1998).

The formation of depurinating adducts specifically at the N-7 of Gua and N-3 of Ade by 1,4-Michael addition to CAT quinone, analogously to those formed by E$_1$(E$_2$)-3,4-Q, suggests that the metabolite CAT may play a major role in tumor initiation by benzene. In fact, CAT is carcinogenic in mice and rats, inducing glandular stomach tumors in these animals. The overall leukemogenicity of benzene could result from a synergistic genotoxic response to CAT quinone, which predominantly produces depurinating DNA adducts, and 1,4-benzoquinone, which produces only stable DNA adducts. (Hirose, M., et al., *Carcinogenesis*, 14, 525-529 (1993); Levay, G., et al., *Carcinogenesis*, 12, 1181-1186 (1991); Levay, G. and Bodell, W. J., *Proc. Natl. Acad. Sci. USA*, 89, 7105-7109 (1992); Robertson, M., et al., *Mutat. Res.*, 249, 201-209 (1990); Smith, M. T., *Environ. Health Perspect.*, 104: *Suppl.* 6, 1219-1225 (1996).

Figure 12:
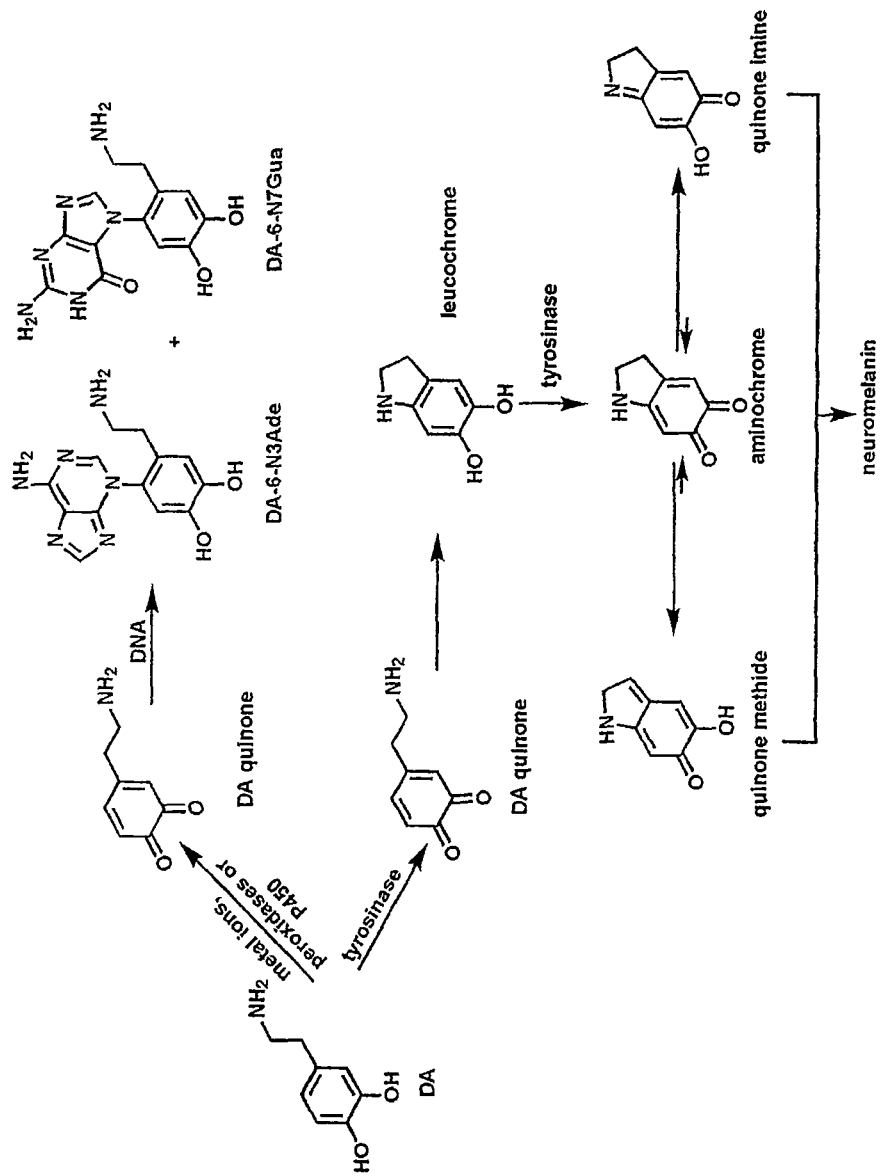
FIG. 12 depicts the metabolism of DA to form neuromelanin or depurinating DNA adducts.

One of the functions of the neurotransmitter DA or its precursor, L-Dopa, is the synthesis of neuromelanin. This occurs by oxidation of DA to its o-quinone, followed by intramolecular cyclization of the nucleophilic amino group via a 1,4-Michael addition (FIG. 12). The product, leucochrome, is further oxidized to aminochrome, which, after tautomerization to its quinone methide and quinone imine, polymerizes to neuromelanin, the pigment of the substantia nigra. Disregulation of DA compartmentalization may lead to DA quinone formation by various oxidants. Under these circumstances, intermolecular 1,4-Michael addition of the N-7 of Gua or N-3 of Ade in DNA to DA quinone could compete successfully with the intramolecular cyclization of DA quinone that leads to dihydroindole derivatives (FIG. 12). In fact, DA cyclizes at a slower rate than L-Dopa and epinephrine. Thus, if oxidation of DA to its quinone does not occur in a properly controlled environment, then perhaps the quinone will react with DNA to form depurinating DNA adducts, generating mutations that could initiate neurodegenerative disorders such as Parkinson's disease. (Hastings, T. G., *J. Neurochem.*, 64, 919-924 (1995); Mattammal, M. B., et al., *J. Neurochem.*, 64, 1845-1854 (1995); Kalyanaraman, B., et al, *Environ. Health Perspect.*, 64, 185-194 (1985); Kalyanaraman, B., et al., *J. Biol. Chem.*, 259, 7584-7589 (1984); Pelizzetti, E., et al., *J. Chem. Soc. Perkins II*, 1651-1655 (1976).)

Conclusions

The o-benzoquinones formed in the metabolism of natural and synthetic estrogens, benzene, and DA react with DNA via 1,4-Michael addition to form specific depurinating adducts that may lead to critical mutations responsible for initiating many cancers and neurodegenerative diseases. Recognition of this proposed unifying mechanism in the etiology of these diseases may provide unique opportunities to develop strategies to assess risk and to prevent diseases.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for inhibiting depurinating DNA adduct formation in cells of a mammal comprising administering to the mammal an effective amount of N-acetylcysteine or a pharmaceutically acceptable salt thereof and resveratrol or a pharmaceutically acceptable salt thereof.

2. A method for inhibiting depurinating DNA adduct formation in breast cells in a mammal comprising administering to the mammal an effective amount of a combination of N-acetylcysteine, melatonin, resveratrol and lipoic acid or pharmaceutically acceptable salts thereof.

3. The method of claim 1 wherein the mammal has a cancer selected from the group consisting of thymoma, lymphoma, sarcoma, lung cancer, liver cancer, brain cancer, non Hodgkin's lymphoma, Hodgkins lymphoma, leukemias, uterine cancer, cervical cancer, bladder cancer, rectal cancer, kidney cancer, colon cancer, and adenocarcinomas such as breast cancer, prostate cancer, ovarian cancer, and pancreatic cancer.

4. The method of claim 1 further comprising administering an effective amount of a melatonin or a pharmaceutically acceptable salt thereof.

5. The method of claim 1 further comprising administering an effective amount of resveratrol.

6. The method of claim 1 further comprising administering and effective amount of lipoic acid.

* * * * *